US010932961B2

(12) United States Patent
Goda et al.

(10) Patent No.: US 10,932,961 B2
(45) Date of Patent: Mar. 2, 2021

(54) ABSORBENT ARTICLE

(71) Applicant: UNICHARM CORPORATION, Ehime (JP)

(72) Inventors: Hiroki Goda, Kagawa (JP); Masashi Yamaguchi, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 347 days.

(21) Appl. No.: 15/757,721

(22) PCT Filed: Jul. 1, 2016

(86) PCT No.: PCT/JP2016/069714
§ 371 (c)(1),
(2) Date: Mar. 6, 2018

(87) PCT Pub. No.: WO2017/043162
PCT Pub. Date: Mar. 16, 2017

(65) Prior Publication Data
US 2019/0038480 A1 Feb. 7, 2019

(30) Foreign Application Priority Data
Sep. 7, 2015 (JP) .............................. JP2015-176177

(51) Int. Cl.
A61F 13/536 (2006.01)
A61F 13/533 (2006.01)
(Continued)

(52) U.S. Cl.
CPC ...... A61F 13/536 (2013.01); A61F 13/15707 (2013.01); A61F 13/533 (2013.01);
(Continued)

(58) Field of Classification Search
CPC .................. A61F 13/536; A61F 13/533; A61F 13/15707; A61F 2013/49084;
(Continued)

(56) References Cited

U.S. PATENT DOCUMENTS 4,762,521 A * 8/1988 Roessler ................. A61L 15/60
604/385.26
5,128,193 A * 7/1992 Anapol ................. A61F 13/533
156/209

(Continued)

FOREIGN PATENT DOCUMENTS

EP 2277483 A1 1/2011
JP 2010-233839 A 10/2010

(Continued)

OTHER PUBLICATIONS

International Search Report issued in PCT/JP2016/069714, dated Sep. 20, 2016, 3 pages.

*Primary Examiner* — Susan S Su
(74) *Attorney, Agent, or Firm* — Hauptman Ham, LLP

(57) ABSTRACT

An absorbent article has a length direction, a width direction and a thickness direction, and is provided at least with an absorbent body including water-absorbent fibers. The absorbent body includes deformation-guiding portions which extend in a predetermined direction, and base portions provided on both sides of each deformation-guiding portion. The deformation-guiding portions are provided with compressed regions which extend in said predetermined direction and in which the absorbent body has been compacted in the thickness direction, and protruding portions which extend in the predetermined direction on both sides of each compressed region and which protrude from the base portion toward the skin surface. The configuration is such that the fiber density of the protruding portions is less than the fiber density of the base portion.

8 Claims, 12 Drawing Sheets

(51) Int. Cl.
*A61F 13/15* (2006.01)
*A61F 13/49* (2006.01)
*A61F 13/531* (2006.01)

(52) U.S. Cl.
CPC ............ *A61F 2013/49084* (2013.01); *A61F 2013/5315* (2013.01)

(58) Field of Classification Search
CPC ........ A61F 2013/5315; A61F 13/49007; A61F 13/537; A61F 13/538; A61F 2013/5349; A61F 2013/53773; A61F 2013/5386; A61F 2013/530131
See application file for complete search history.

(56) References Cited

U.S. PATENT DOCUMENTS

| | | | | |
|---|---|---|---|---|
| 5,817,271 | A | * | 10/1998 | Congleton ........ A61F 13/15707 264/400 |
| 6,362,391 | B1 | * | 3/2002 | Mizutani ........... A61F 13/51108 604/379 |
| 2004/0176734 | A1 | * | 9/2004 | Rasmussen ......... A61F 13/4756 604/380 |
| 2004/0253892 | A1 | * | 12/2004 | Baker .................. B29C 43/222 442/327 |
| 2012/0059342 | A1 | | 3/2012 | Kinoshita et al. |
| 2013/0035656 | A1 | | 2/2013 | Moriya et al. |
| 2013/0267926 | A1 | * | 10/2013 | Uematsu ............. A61F 13/4758 604/385.101 |
| 2015/0057630 | A1 | * | 2/2015 | Tange ................ A61F 13/15203 604/374 |
| 2015/0065975 | A1 | * | 3/2015 | Roe ................... A61F 13/49001 604/369 |
| 2015/0173959 | A1 | * | 6/2015 | Carlucci ................. A61L 15/60 604/367 |
| 2015/0359687 | A1 | | 12/2015 | Goda et al. |

FOREIGN PATENT DOCUMENTS

| | | |
|---|---|---|
| JP | 2011-177306 A | 9/2011 |
| JP | 2012-120707 A | 6/2012 |
| JP | 2014-136126 A | 7/2014 |
| WO | WO-2013018745 A1 * | 2/2013 ......... A61F 13/4756 |

\* cited by examiner

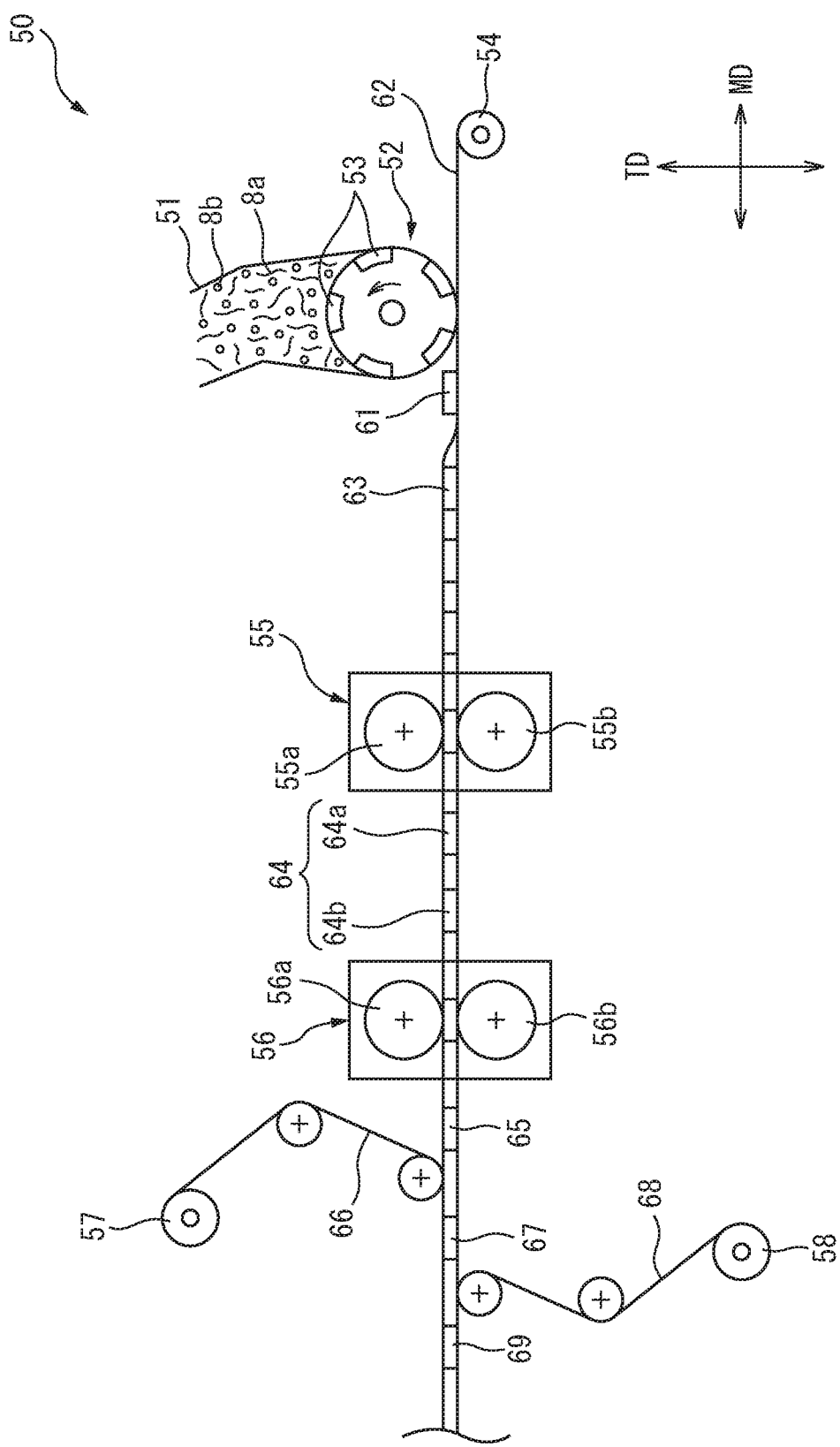

FIG. 12(a)
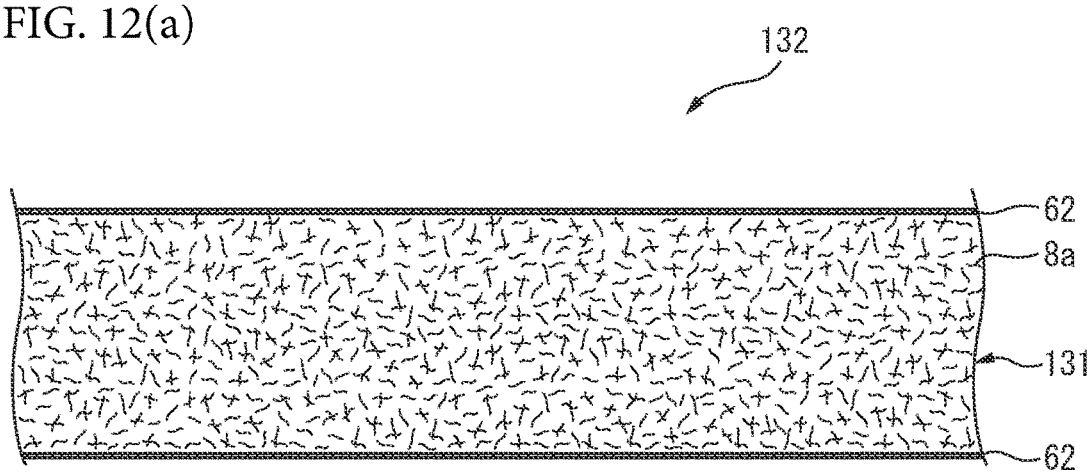
FIG. 12(b)
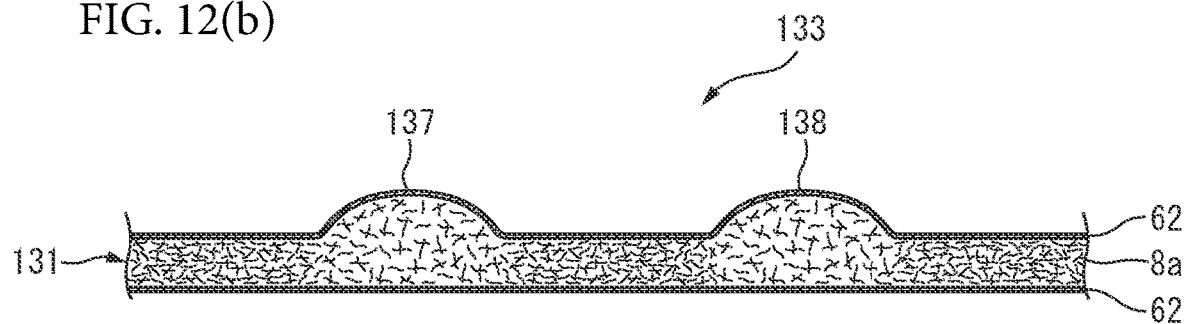
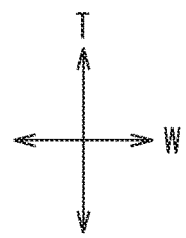

ABSORBENT ARTICLE

RELATED APPLICATIONS

The present application is a National Phase of International Application Number PCT/JP2016/069714, filed Jul. 1, 2016, and claims priority to Japanese Application Number 2015-176177, filed Sep. 7, 2015.

TECHNICAL FIELD

The present disclosure relates to an absorbent article, and especially to a disposable diaper.

BACKGROUND ART

In an absorbent article, various improvements have been made in order to realize preferably comfortable feeling when being worn while preventing the excrement such as urine, etc., from leaking out.

For example, in Patent Literature 1, an absorbent article is disclosed, which includes a liquid permeable top sheet, a liquid impermeable back sheet, and an absorbent body that is provided between the top sheet and the back sheet, and in which a joining portion is formed in which at least the top sheet and the absorbent body are joined, wherein the absorbent body includes a first region in which the absorbent material which configures the absorbent body has a predetermined basis weight, and a second region which has a basis weight of the absorbent material that is less than that of the first region, the second region extends along the longitudinal direction of the absorbent article, and is sandwiched by the first region in the width direction of the absorbent article, and the joining region is formed in the second region.

Further, in Patent Literature 2, an absorbent article is disclosed, which includes a liquid permeable layer, a liquid impermeable layer, an absorbent core which is provided between the liquid permeable layer and the liquid impermeable layer, and a joining portion which joins the liquid permeable layer and the absorbent core, wherein the absorbent core includes hydrophilic fibers and absorbent polymers as an absorbent material, the absorbent core further includes a first region which has a predetermined absorbent material basis weight and a second region which has an absorbent material basis weight that is less than that in the first region, and a ratio of an absorbent polymer basis weight with respect to the absorbent material basis weight in the second region is 10/100 to 47/100, and the joining portion is formed on the inner side in the second region.

CITATION LIST

Patent Literature

PTL 1: Japanese Unexamined Patent Publication No. 2010-233839
PTL 2: Japanese Unexamined Patent Publication No. 2014-136126

SUMMARY OF INVENTION

Technical Problem

In each of the absorbent articles described in Patent Literatures 1 and 2, the absorbent body (the absorbent core) includes a high fiber density region in which the fibers which configure the absorbent body, such as the hydrophilic fibers, etc., have a predetermined basis weight, and a low fiber density region in which the basis weight of the fibers is lower than that in the high fiber density region. Further, the low fiber density region extends along the longitudinal direction of the absorbent article, and is sandwiched by the high fiber density region in the width direction of the absorbent article, and each of the absorbent article has a configuration in which, in the low fiber density region, a compressed portion is provided which is formed by embossing, etc., at least the absorbent body. In such a configuration, when the absorbent article is being worn, the boundary between the compressed portion and the portion other than the compressed portion is to be a portion at which the bending of the absorbent body originates and to be a portion which guides the deformation thereof, due to the rigidity differences, whereby the absorbent body can be deformed in accordance with the body shape or motion of the user, and can absorb and retain excrement with efficiency.

However, in the absorbent articles described in Patent Literatures 1 and 2, since the compressed portion is not only made to be stiff due to the compression of the compressed portion itself, but also is adjacent to and sandwiched by the high fiber density region in which the fiber density is high and is relatively stiff, when the skin comes in contact with the surface of the absorbent article, it is easy for the user to feel the stiffness of the compressed portion and of the high fiber density region. Accordingly, there may have been cases in which the texture is degraded, and the feeling when the absorbent article is worn is deteriorated.

Accordingly, the technical problem to be solved in the present invention is to provide an absorbent article which makes it difficult to feel stiffness and is comfortable when being worn, while being capable of guiding deformation.

Solution to Problem

In order to solve the above mentioned problems, the absorbent article of the present invention, has a longitudinal direction, a width direction, and a thickness direction, and comprises an absorbent body that includes at least a water absorbent fiber, wherein the absorbent body includes a deformation guiding portion which extends in a predetermined direction, and base portions which are disposed on both sides of the deformation guiding portion, the deformation guiding portion includes a compressed region which extends in the predetermined direction and in which the absorbent body is compacted in the thickness direction, and protruded portions which extend in the predetermined direction on both sides of the compressed region and protrude from the base portions toward a skin surface side, and a fiber density of the protruded portions is lower than a fiber density of the base portions.

Effect of Invention

According to the absorbent article of the present invention, the boundary between the compressed region and the protruded portions of the deformation guiding portion is to be a portion at which the bending originates due to the rigidity differences, whereby makes it possible to guide the deformation of the absorbent body, and the absorbent article, so as to be stably deformed into a suitable shape. Further, since the protruded portions are provided on both sides in the direction in which the compressed region of the deformation guiding portion extends, so as to protrude toward the skin surface side, in which the fiber density is lower than that in the base portion and are relatively soft, when the skin surface of the user comes in contact with the surface of the absorbent article, there are many opportunities to come in contact with the protruded portions, whereby it is easy for the user to feel the softness of the protruded portions. Further, when the absorbent article is deformed so as to protrude toward the non-skin surface side, the protruded portions come closer to each other, and cover the compressed region in which the stiffness is increased by compression, whereby even the skin surface of the user comes in contact with the surface of the absorbent article, it is difficult to be in contact with the compressed region, and for the user to feel the stiffness of the compressed region. As a result, an excellent feeling when being worn can be obtained by the absorbent article as a whole.

BRIEF DESCRIPTION OF DRAWING

FIG. 5 is a schematic view of a manufacturing apparatus to be used in a manufacturing method of the absorbent article of the first embodiment according to the present invention.

FIG. 12(a) is a main portion enlarged end view of a second laminated body, and FIG. 12(b) is a main portion enlarged end view of third laminated body after being shaped in a third step, which are formed in the manufacturing method of the absorbent article of the second embodiment according to the present invention.

DESCRIPTION OF EMBODIMENTS

Figure 1:
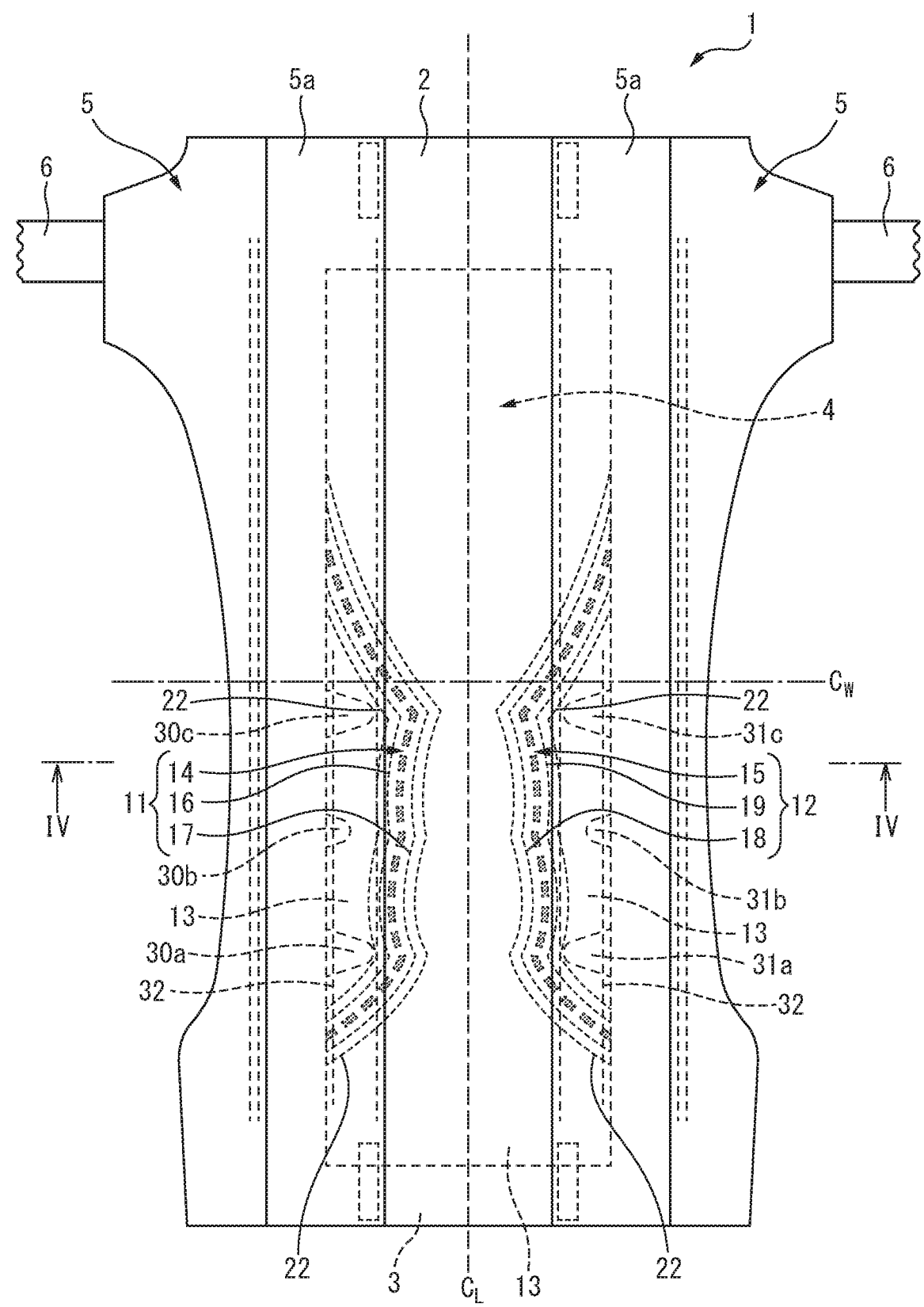
FIG. 1 is a plan view which schematically shows an expanded state of a first embodiment of a disposable diaper as an absorbent article according to the present invention.

The present invention relates to the following aspects.

[Aspect 1] An absorbent article which has a longitudinal direction, a width direction, and a thickness direction, and comprises an absorbent body that includes at least a water absorbent fiber, wherein the absorbent body includes a deformation guiding portion which extends in a predetermined direction, and base portions which are disposed on both sides of the deformation guiding portion, the deformation guiding portion includes a compressed region which extends in the predetermined direction and in which the absorbent body is compacted in the thickness direction, and protruded portions which extend in the predetermined direction on both sides of the compressed region and protrude from the base portions toward a skin surface side, and a fiber density of the protruded portions is lower than a fiber density of the base portions.

According to aspect 1, the boundary between the compressed region and the protruded portions of the deformation guiding portion is to be a portion at which the bending originates, whereby makes it possible to stably guide the deformation of the absorbent body, and the absorbent article, so as to stably deform the same into a suitable shape. Further, since the protruded portions are provided on both sides in the direction in which the compressed region of the deformation guiding portion extends, so as to protrude toward the skin surface side, in which the fiber density is lower than that in the base portion and is relatively soft, when the skin surface of the user comes in contact with the surface of the absorbent article, there are many opportunities to come in contact with the protruded portions, whereby it is easy for the user to feel the softness of the protruded portions. Further, when the absorbent article is deformed so as to protrude toward the non-skin surface side, the protruded portions come closer to each other, and cover the compressed region in which the stiffness is increased by compression, whereby even the skin surface of the user comes in contact with the surface of the absorbent article, it is difficult to be in contact with the compressed region, and for the user to feel the stiffness of the compressed region. As a result, an excellent feeling when being worn can be obtained by the absorbent article as a whole.

[Aspect 2] The absorbent article according to aspect 1, wherein the predetermined direction is the longitudinal direction, and the absorbent body includes the deformation guiding portions so as to sandwich a width direction central axis line of the absorbent body, at positions mutually being separated from each other.

According to aspect 2, by deforming the absorbent body along the deformation guiding portions, a box-shaped three dimensional space which opens to the skin side of the user, whereby the excrement of the user can be received reliably and stably, and it is difficult for the excrement to come in contact with the skin of the user, so as to improve the feeling when the absorbent article is being worn.

[Aspect 3] The absorbent article according to aspect 2, wherein the absorbent body includes a longitudinal direction, a width direction, and a thickness direction, and is configured by including an absorbent core which includes at least the water absorbent fiber, and a core wrapping sheet which covers an outer circumferential surface of the absorbent core, the absorbent core includes a plurality of bending guiding lines which are disposed in parallel in the longitudinal direction, each of which connecting portions of a pair of notch portions that are provided at both end portions in the width direction at symmetrical positions so as to sandwich the width direction central axis line, the portions of the pair of notch portions being the closest to the width direction central axis line, and the deformation guiding portion extends over at least, from the bending guiding line which is the closest to one end in the longitudinal direction of the absorbent core among the plurality of bending guiding lines, to the bending guiding line which is the closest to the other end in the longitudinal direction of the absorbent core among the plurality of bending guiding lines.

According to aspect 3, by the plurality of bending guiding lines which are disposed in parallel in the longitudinal direction of the absorbent core, it is easy for the absorbent core to be bent in the longitudinal direction, and by the pair of notch portions which are provided at both end portions in the width direction of the absorbent core, when the absorbent body is deformed and to be three dimensional along the deformation guiding portion and the bending guiding lines, the interference between the end portions of the absorbent body can be prevented, whereby the absorbent body can be deformed with accuracy so as to form the above mentioned box-shaped three dimensional space, and to more reliably secure the space to house the excrement. As a result, the absorbent article of aspect 3 makes it difficult for the excrement to be in contact with the skin of the user, whereby the feeling when the absorbent article is being worn is even more improved.

[Aspect 4] The absorbent article according to any one of aspects 1 to 3, wherein a width of the compressed region is ½ or shorter of a width of the deformation guiding portion.

According to aspect 4, by arranging the ratio of the width of the compressed region with respect to the width of the deformation guiding portion, when the absorbent article is deformed so as to protrude toward the non-skin surface side, the protruded portions are to come closer to each other, whereby it is even easier for the compressed portion in which the stiffness is increased by the compression to be covered, and when the skin surface of the user comes in contact with the surface of the absorbent article, it is difficult to feel the stiffness of the compressed portion. As a result, the texture of the absorbent article is even more improved.

[Aspect 5] The absorbent article according to any one of aspects 1 to 4, wherein the compressed region includes a plurality of compressed portions which are provided intermittently and serially in the predetermined direction, and non-compressed portions each of which being provided between the adjacent compressed portions.

According to aspect 5, the compressed region is intermittently provided with the compressed portions, whereby in the compressed region, the ratio of the portion in which the stiffness is increased by the compression is lower than that in the case in which the compressed portions are continuously provided, and the opportunities for the skin to be in contact with the portion in which the stiffness is increased by the compression are decreased, and thus it is difficult for the user to feel the portion with stiffness. Further, the compressed region includes the non-compressed portions which are not compressed and are in a state of being softer than the compressed portions, in between the adjacent compressed portions, whereby the feeling is excellent when the deformation guiding portion of the absorbent article is felt along the longitudinal direction through the top sheet. Accordingly, an even softer texture can be obtained.

[Aspect 6] The absorbent article according to any one of aspects 1 to 5, wherein the absorbent body includes absorbent polymers, and a basis weight of the absorbent polymers included in the deformation guiding portion is less than a basis weight of the absorbent polymers included in the base portions.

According to aspect 6, since the basis weight of the absorbent polymers included in the deformation guiding portion is less than that in the base portions, when the absorbent body absorbs liquid excrement, the expansion of the deformation guiding portion due to the swelling of the absorbent polymers is smaller than that of the base portions. Accordingly, it is difficult for the deformation of the absorbent article which originates at the boundary between the deformation guiding portion, especially the compressed region and the protruded portions to be inhibited, whereby the deformed state of the absorbent article can be stably maintained even after the absorbent body absorbed liquid excrement.

[Aspect 7] The absorbent article according to any one of aspects 1 to 6, wherein each of the base portions includes a recessed portion which is recessed toward a non-skin surface side, and is provided adjacent to the protruded portion along a longitudinal direction of the protruded portion.

According to aspect 7, the recessed portion of the base portions is provided in a state of being adjacent to the protruded portions, whereby the difference of the thicknesses between the protruded portions and the base portions is larger, and when the absorbent article is being worn, it is easier for the user to feel the protruded portions which are softer than the compressed region and the base portions, and thus the soft texture is even more improved. Further, since the recessed portion itself is to be a portion at which the bending of the absorbent body originates, the absorbent article can be even more stably deformed.

[Aspect 8] The absorbent article according to aspect 7, wherein the absorbent body includes absorbent polymers, and a mass inclusion ratio of the absorbent polymers included in a portion which extends in the thickness direction on the non-skin surface side of the recessed portion in each of the base portions is more than a mass inclusion ratio of the absorbent polymers included in a portion other than the portion which extends in the thickness direction on the non-skin surface side of the recessed portion in each of the base portions.

According to aspect 8, the portion of the recessed portion of the base portions which extends in the thickness direction on the non-skin surface side makes it easier for the protruded portions to be felt even when the absorbent polymers are swollen, and further makes it possible to stably secure the absorbability in the vicinity of the protruded portions, since the recessed portion is recessed toward the non-skin surface side.

Hereinbelow, the absorbent article according to the present invention is explained in detail based on the drawings.

Incidentally, in the present description, unless otherwise noted, "viewing an object (for example, an absorbent article, an absorbent body, etc.) which is placed on a horizontal plane in an expanded state, from the upper side in a vertical direction, in a thickness direction of the object" is simply referred to as "a plan view".

Further, in the present description, "a width direction W" means "a width direction (a transverse direction) of an object in a plan view", "a longitudinal direction L" means "a longitudinal direction of an object in a plan view", "a thickness direction T" means "a thickness direction of an object which is placed on a horizontal plane in an expanded state", and the width direction W, the longitudinal direction L, and thickness direction T are in a relationship of being mutually orthogonal to each other.

Further, in the present description, "a relatively closer side to the width direction central axis line $C_L$ which extends in the longitudinal direction L, in the width direction W of a longitudinal object (for example, an absorbent article, an absorbent body, etc.)" is referred to as "an inner side in the width direction", and "a relatively farther side to the width direction central axis line $C_L$, in the width direction W of a longitudinal object" is referred to as "an outer side in the width direction". Further, a longitudinal direction central axis line which extends in the width direction W, in the longitudinal direction L of a longitudinal object is referred to as a longitudinal direction central axis line $C_W$.

Further, in the present description, "a relatively closer side to the skin surface of a wearer, in the thickness direction T of an absorbent article" is referred to as "a skin surface side", and "a relatively farther side to the skin surface of a wearer, in the thickness direction T of an absorbent article" is referred to as "a non-skin surface side".

FIGS. 1 to 4 are views which show the first embodiment of the absorbent article of the present invention, and in the first embodiment, a case in which the absorbent article is a disposable diaper is explained.

That is, the disposable diaper 1 includes the longitudinal direction L, the width direction W and the thickness direction T, and further includes a liquid permeable top sheet 2, a liquid impermeable back sheet 3, and an absorbent body 4 which is disposed between the top sheet 2 and the back sheet 3. Further, the disposable diaper 1 includes side sheets 5, 5 which form a pair of leakage barriers 5a, 5a and have hydrophobic or water repellent property. Incidentally, in FIG. 1, one end side in the longitudinal direction L which is positioned downward in FIG. 1 is the ventral side which covers the abdomen of the user, and the other end side in the longitudinal direction L which is positioned upward is the dorsal side which covers the back (the buttocks) of the user. Further, the disposable diaper 1 of the present embodiment is a so-called tape type disposable diaper which is attached to the user by using a tape fastener 6, when being worn.

Incidentally, the absorbent article according to the present invention is not limited to the above mentioned tape type disposable diaper, and may also be a so-called shorts type disposable diaper which has a shorts type shape before being worn.

Figure 4:
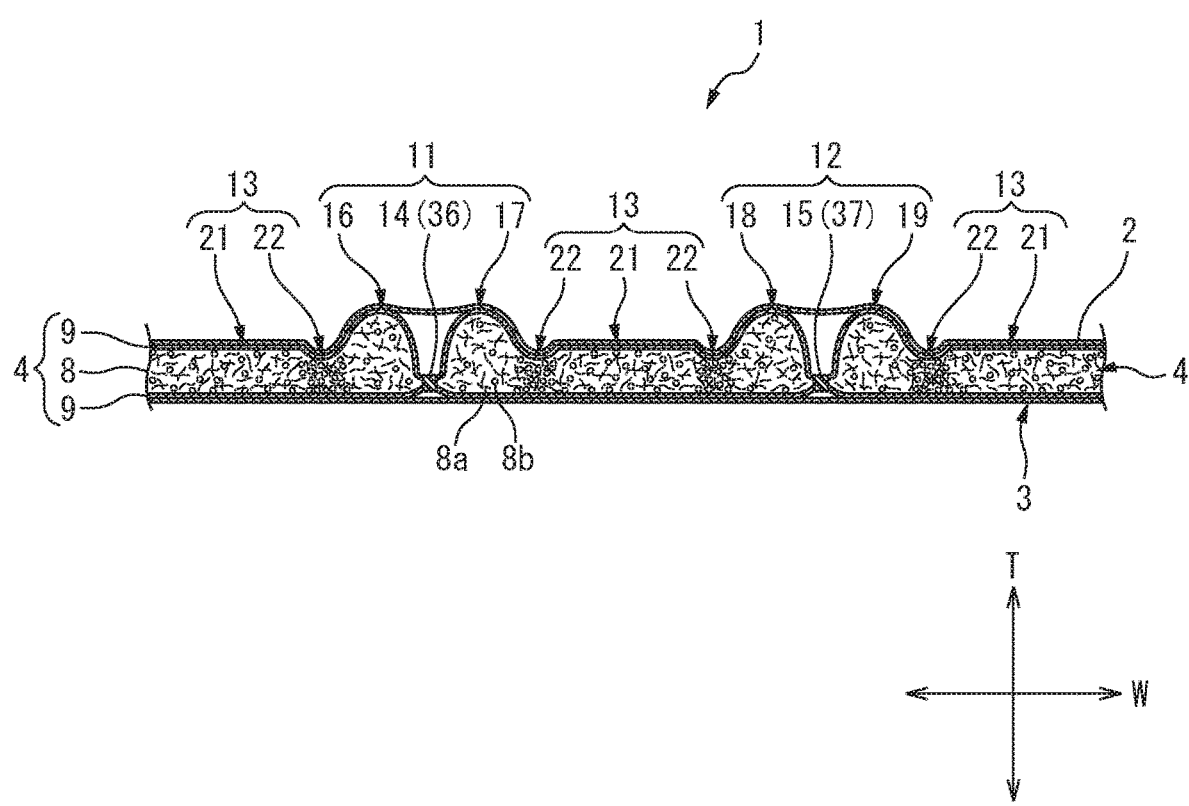
FIG. 4 is a schematic main portion enlarged end view along IV-IV line shown FIG. 1. Note that leakage barriers are omitted.

The top sheet 2 quickly absorbs liquid excrement of the user such as urine, etc., or let the liquid excrement quickly permeate therethrough and transfers the liquid excrement to the absorbent body 4, and is disposed on the surface side which faces the skin of the user in the absorbent body 4 (that is, in FIG. 4, the upper surface side of the absorbent body 4).

In the present embodiment, the top sheet 2 is formed so as to be long along the longitudinal direction L of the disposable diaper 1.

The top sheet 2 may be formed by, for example, a nonwoven fabric, a woven fabric, a synthetic resin film in which liquid permeable holes are formed, a net-like sheet with meshes, etc., and may preferably be formed by a nonwoven fabric.

The back sheet 3 is provided on the outer side in the disposable diaper 1 (that is, in FIG. 4, the lower surface side of the absorbent body 4), and prevents permeation of the discharged excrement and also prevents the discharged excrement from leaking outside.

The back sheet 3 is mutually joined to the top sheet 2 in a state in which the absorbent body 4 is disposed in between. As the joining means, an arbitrary means, such as for example, adhesion by a hot melt type adhesive agent, joining by heat embossing treatment, joining by ultrasonic embossing treatment, etc., may be used.

Incidentally, in the present invention, as the back sheet, for example, a nonwoven fabric which is subjected to a waterproof treatment, a synthetic resin film such as polyethylene, polypropylene, etc., a composite sheet of a nonwoven fabric and a synthetic resin film (for example, a composite film in which a breathable synthetic resin film is joined to a nonwoven fabric such as a spunbond, spunlace, etc.), an SMS nonwoven fabric in which a highly water resistant meltblown nonwoven fabric is sandwiched by strong spunbonded nonwoven fabrics, etc., may be used.

The absorbent body 4 is formed in a substantially rectangular shape as a whole in a plan view, and in the present embodiment, is configured by including an absorbent core 8 which includes at least water absorbent fibers 8a that absorb and retain liquid excrement, and a core wrapping sheet 9 which covers the outer circumferential surface of the absorbent core 8. Further, as shown in FIG. 1, the absorbent body 4 as a whole is disposed so as to be shifted more to the ventral side than to the dorsal side of the disposable diaper 1.

Incidentally, as the water absorbent fiber which forms the absorbent core, for example, a cellulose type water absorbent fiber such as pulp, etc., is preferably used, and further, the core wrapping sheet is not particularly limited as long as the core wrapping sheet has a liquid permeability and absorbent body retaining property, however, tissue, etc., is preferably used.

Further, in the present embodiment, in the absorbent core 8 of the absorbent body 4, absorbent polymers 8b are included in addition to the water absorbent fibers 8a. As such absorbent polymers, for example, super absorbent materials of a starch type, a cellulose type, a synthetic polymer type, may be used.

The absorbent body 4 includes a pair of deformation guiding portions 11, 12 which guides the deformation of the absorbent body 4, and the disposable diaper 1, to a predetermined shape, and extend in a predetermined direction (in the present embodiment, in the longitudinal direction L of the disposable diaper 1), and the base portions 13 which are disposed on both sides of the deformation guiding portions 11, 12.

Further, the deformation guiding portion 11 (12) includes a portion in which the absorbent body 4 is compressed in the thickness direction, that is, one compressed region 14 (15) which extends in the predetermined direction, that is, in the longitudinal direction of the deformation guiding portion 11 (12), and further includes protruded portions 16, 17 (18, 19) which extend in the predetermined direction, that is, in the longitudinal direction of the deformation guiding portion 11 (12) on both sides in the longitudinal direction of the compressed region 14 (15) and protrude from the base portions 13 toward the skin surface side.

Incidentally, in the present description, a state in which the absorbent body is compressed means that the absorbent body includes a portion being compacted in the thickness direction, the core wrapping sheets which are present on the top sheet side and on the back sheet side are joined to each other through the compacted portion, the thickness of the compacted portion is thinner than portions which are not compacted, and the fiber density of the absorbent core in the compacted portion is higher than the fiber density of the absorbent core in the portions which are not compacted.

In the present embodiment, the pair of deformation guiding portions 11, 12 and the base portions 13 in the absorbent body 4 are integrally formed by the absorbent core 8 and the core wrapping sheet 9.

Incidentally, the basis weight (the basis weight of the water absorbent fibers 8a and the basis weight of the absorbent polymers 8b in total) of the base portions in the absorbent body of the present invention may differ according to usage, however, may preferably be 100 to 1000 g/m$^2$, and may more preferably be 200 to 900 g/m$^2$, and may even more preferably be 300 to 800 g/m$^2$. When the basis weight of the base portions in the absorbent body is 100 g/m2 or more, the absorption capacity of the base portions can be reliably secured which mainly performs absorption and retention of the liquid excrement in the absorbent body, and when the basis weight of the base portions in the absorbent body is 1000 g/m2 or less, the base portions are not too bulky, and comfortable feeling when being worn can be obtained.

On the other hand, the basis weight of the deformation guiding portion in the absorbent body may preferably be 30 to 80 mass % of the basis weight of the base portions. By arranging the basis weight of the deformation guiding portion to 30 mass % or more of the basis weight of the base portions, the possibility of shape collapse of the absorbent body from the deformation guiding portion can be suppressed, and by arranging the basis weight of the deformation guiding portion to 80 mass % or less of the basis weight of the base portions, the deformation guiding portion is not too bulky, and comfortable feeling when being worn can be obtained.

Figure 3:
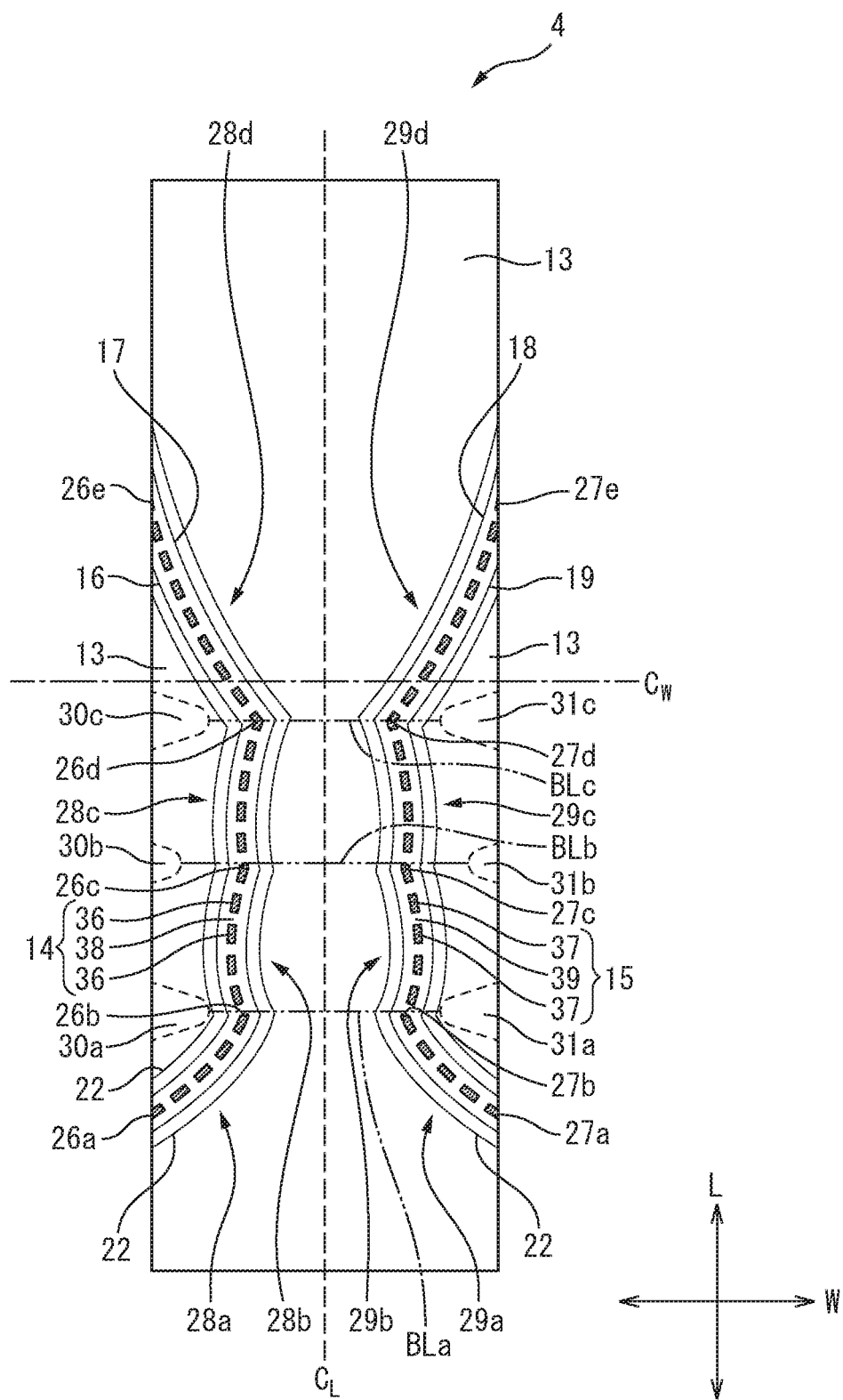
FIG. 3 is a plan view which schematically shows an absorbent body to be used in the disposable diaper of FIG. 1.

As shown in FIGS. 1, 3 and 4, each of the base portions 13 includes, in the present embodiment, a flat portion 21 in which the surface on the skin surface side is formed into a flat surface, and recessed portions 22 which are recessed toward the non-skin surface side and is opened to the skin surface side. Incidentally, the portion other than the deformation guiding portions 11, 12 in the absorbent body 4 is basically the base portions 13. Further, the flat portion 21 as a whole has a substantially constant thickness.

Each of the recessed portions 22 is, as shown in FIG. 4, in the present embodiment, formed into a substantially U-shaped cross section, thinner than the flat portion 21, and further is in a state in which the top sheet 2 is disposed along the surface recessed at the recessed portions 22. Further, each of the recessed portions 22 is adjacent to either one of the protruded portions 16 to 19 of the deformation guiding portions 11, 12, and is disposed so as to extend in the same direction as the longitudinal direction of the protruded portions 16 to 19, so as to be along the longitudinal direction of the adjacent protruded portions 16 to 19.

In this manner, since each of the recessed portions 22 of the base portions 13 is provided in a state of being adjacent to the protruded portions 16 to 19, the difference of the thicknesses between the protruded portions 16 to 19 and the base portions 13 is to be larger. Accordingly, when the disposable diaper 1 is being worn, the opportunities for the user to come in contact with the soft protruded portions 16 to 19 is even more increased, and as described later, it is easier for the user to feel the protruded portions 16 to 19 which are softer than the compressed regions 14, 15 and the base portions 13, and thus the soft texture is even more improved. Further, since each of the recessed portions 22 itself is to be a portion at which the bending of the absorbent body 1 originates, the absorbent article 1 can be even more stably deformed.

On the other hand, the pair of deformation guiding portions 11, 12 are disposed so as to sandwich the axis line in the longitudinal direction L of the absorbent body 4, at positions mutually being separated from each other. The pair of deformation guiding portions 11, 12 are, when viewing the absorbent body 4 in a plan view, formed into a shape symmetrical with respect to the width direction central axis line $C_L$ which extends in the longitudinal direction L.

As shown in FIGS. 1 and 3, each of the deformation guiding portions 11, 12 of the present embodiment as a whole has a shape so as to protrude toward the width direction central axis line $C_L$ which extends in the longitudinal direction L of the absorbent body 4. To be more specific, the deformation guiding portions 11, 12 respectively include first portions 28a, 29a, which extend on an inner side in the width direction and in the direction toward end portions on the dorsal side of the absorbent body 4, with end portions closest in the width direction W of the absorbent body 4 at positions close to end portions on the ventral side of the absorbent body 4 as starting points 26a, 27a, and reach first base points 26b, 27b which are positioned between the end portions in the width direction W of the absorbent body and the width direction central axis line $C_L$ which extends in the longitudinal direction L, in a gently curved state so as to protrude toward the inner side in the width direction of the absorbent body 4. Further, the deformation guiding portions 11, 12 respectively include second portions 28b, 29b which reach second base points 26c, 27c which are positioned on the further dorsal side of the absorbent body 4 than the first base points 26b, 27b, from the first base points 26b, 27b, while gently being curved so as to protrude toward the outer side in the width direction of the absorbent body 4, and third portions 28c, 29c which are positioned on the further dorsal side of the absorbent body 4 than the second base points 26c, 27c, from the second base points 26c, 27c, while gently being curved so as to protrude toward the outer side in the width direction of the absorbent body 4. Still further, the deformation guiding portions 11, 12 respectively include fourth portions 28d, 29d, which reach end points 26e, 27e that are positioned on the further dorsal side than third base points 26d, 27d and are positioned at end portions closest in the width direction W of the absorbent body 4, from the third base points 26d, 27d, in a gently curved state so as to protrude toward the outer side in the width direction of the absorbent body 4.

Incidentally, the first to the third base points are disposed, so that the distance between the second base points 26c, 27c is shorter than the distance between the first base points 26b, 27b of the one deformation guiding portion 11 and the other deformation guiding portion 12, and further, the distance between the third base points 26d, 27d is shorter than the distance between the second base points 26c, 27c.

Figure 2:
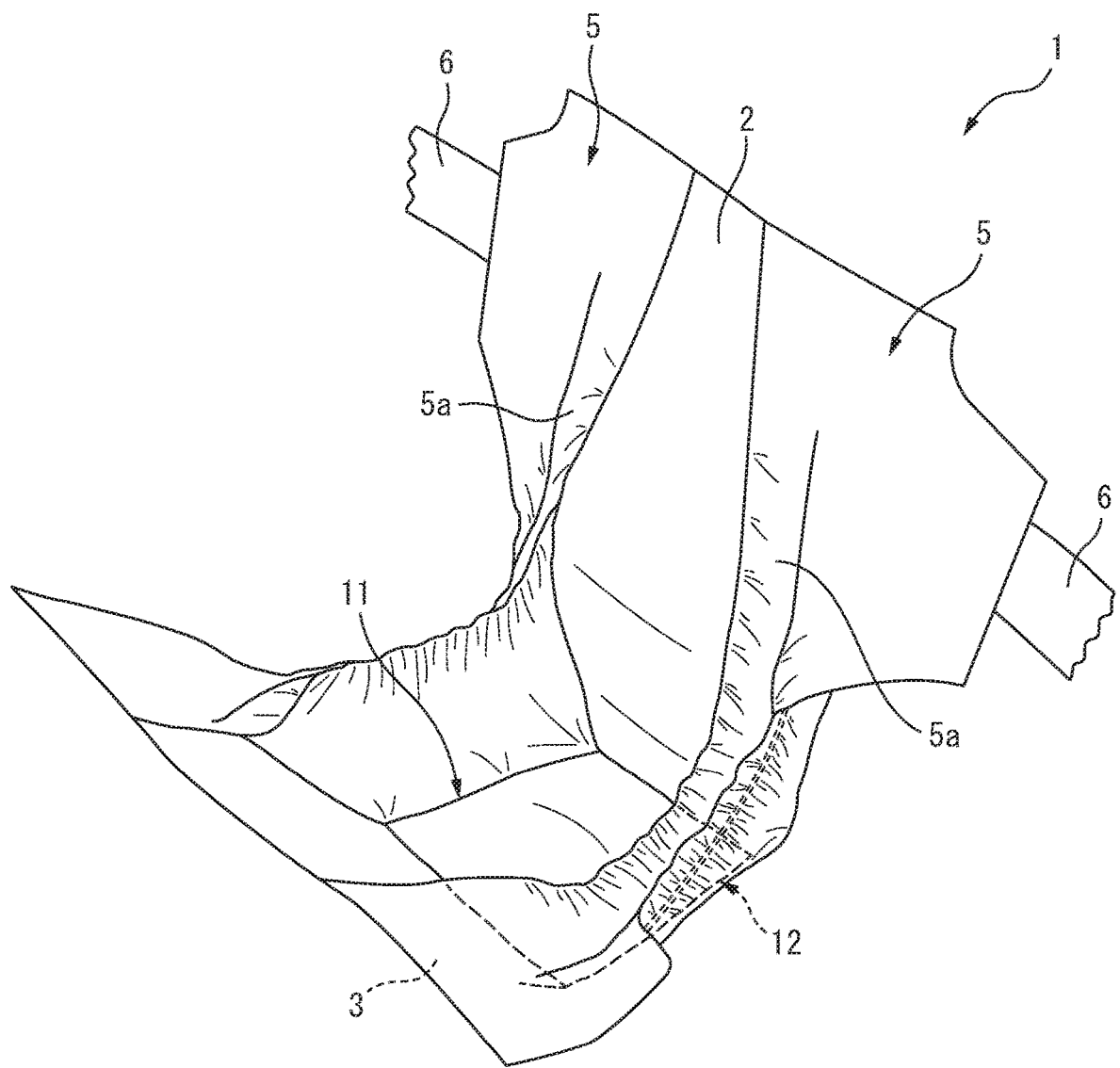
FIG. 2 is a perspective view which schematically shows a state in which the disposable diaper of FIG. 1 is guided to be deformed at the deformation guiding portion.

Further, when the user wears the disposable diaper 1, as shown in FIG. 2, the absorbent body 4 and further, the disposable diaper 1 are to be bent in a valley fold so that the top sheet 2 is placed on the inner side, along the first to the fourth portions 28a to 28d, 29a to 29d of the pair of deformation guiding portions 11, 12, whereby the absorbent body 4 can form a box-shaped three dimensional space which is opened to the skin surface side of the user. Accordingly, the excrement of the user can be received reliably and stably, and it is difficult for the excrement to come in contact with the skin of the user, so as to improve the feeling when the absorbent article is being worn.

Further, in the present embodiment, as shown in FIG. 3, the absorbent core 8 which configures the absorbent body 4 includes the longitudinal direction L, the width direction W, and the thickness direction T, and is provided with notch portions 30 (30a to 30c), 31 (31a to 31c) which are formed by portions of the edge portions of the absorbent core 8 being cut out, at respective positions corresponding to the first base points to the third base points 26b to 26d, 27b to 27d, at both end portions in the width direction W. Each of the notch portions 30, 31 has a tapered shape so as to protrude toward the width direction central axis line $C_L$, and by the notch portions 30, 31 being formed in such a shape, the rigidity differences in the longitudinal direction of the absorbent core 8 is made, and thus the bending guiding lines can be easily oriented. As a result, when the absorbent body 4 is deformed and to be three dimensional, since the bending range in which the end portions of the absorbent body 4 do not interfere with each other can be broadly secured, the absorbent body 4 can be even more easily deformed to a predetermined shape.

Further, in the present embodiment, the notch portions 30, 31 are not provided in the core wrapping sheet 9 which configures the absorbent body 4. By the notch portions 30, 31 not being provided in the core wrapping sheet 9, the outer circumferential surface of the absorbent core 8 can be reliably covered, and can prevent the absorbent polymers 8b inside the absorbent core 8 from leaking out.

Incidentally, in the absorbent body which configures the absorbent article, the notch portion can take an arbitrary shape, such as a polygon, an arc shape, etc., as long as the notch portion can prevent the interference between the end portions of the absorbent body. Further, the above description does not prevent the core wrapping sheet which configures the absorbent body from being provided with the notch portion.

Further, the absorbent core 8 is, as shown in FIG. 3, provided with three bending guiding lines BLa to BLc which are disposed in parallel in the longitudinal direction L, each of which connecting portions of the pair of notch portion 30, 31 that are provided at both end portions in the width direction W at symmetrical positions so as to sandwich the width direction central axis line $CA_L$, the portions of the pair of notch portion 30, 31 being the closest to the width direction central axis line $CA_L$, and the deformation guiding portions 11, 12 extend at least from the bending guiding line BLa which is the closest to the one end in the longitudinal direction L of the absorbent core 8 (which corresponds to the ventral side end portion of the absorbent body 4) to the bending guiding line BLc which is the closest to the other end in the longitudinal direction L of the absorbent core 8 (which corresponds to the dorsal side end portion of the absorbent body 4).

The absorbent core 8 configured in this manner can be easily bent in the longitudinal direction L by the three bending guiding lines BLa to BLc which are disposed in parallel in the longitudinal direction L, and the interference between the end portions of the absorbent body 4 can be prevented, when the absorbent body 4 is deformed along the deformation guiding portions 11, 12 and the bending guiding lines BLa to BLc and to be three dimensional, by the pair of notch portions 30, 31 which are provided at both end portions in the width direction W of the absorbent core 8, whereby the absorbent body 4 which is configured by such absorbent core 8 can be even more easily deformed with accuracy, so as to form the above mentioned box-shaped three dimensional space.

Incidentally, in the present embodiment, three of the bending guiding lines BLa to BLc are disposed in parallel in the longitudinal direction L of the absorbent core 8, however, in the present invention, the number of the bending guiding lines is not particularly limited, and two of the bending guiding lines may be disposed in parallel in the longitudinal direction of the absorbent core, or four or more of the bending guiding lines may be disposed in parallel. Note that when three or more of the bending guiding lines are disposed in parallel in the longitudinal direction of the absorbent core, a polyhedral excrement housing space with more surfaces can be formed, whereby the excrement of the user can be received reliably and stably, and it is difficult for the excrement to come in contact with the skin of the user, so as to further improve the feeling when the absorbent article is being worn.

Further, in the present embodiment, the one end in the longitudinal direction L of the absorbent core 8 which is positioned on the lower side in FIG. 1 is the end portion on the ventral side which covers the abdomen of the wearer, and the other end in the longitudinal direction L of the absorbent core 8 which is positioned on the upper side in FIG. 1 is the end portion on the dorsal side which covers the back (the buttocks) of the wearer, however, the present invention is not limited to this embodiment, and the one end may be the end portion on the ventral side and the other end may be the end portion on the dorsal side, according to the types, etc., of the absorbent article.

Further, as shown in FIG. 1, in order for the deformation guiding portions 11, 12 to more easily be in a valley folded state so that the top sheet 2 is placed on the inner side, elastic members 32 are respectively disposed along the longitudinal direction of the absorbent body 4, in the vicinity of the both edge portions in the width direction W of the absorbent body 4 of the disposable diaper 1.

The compressed region 14 (15) of the deformation guiding portion 11 (12) is formed by compressing the absorbent body 4, that is, portions of the absorbent core 8 and the core wrapping sheet 9 in the thickness direction, by embossing treatment, etc., and one compressed region 14 (15) is disposed between two protruded portions 16, 17 (18, 19), and further, two protruded portions 16, 17 (18, 19) are formed along the one compressed region 14 (15).

To be more specific, the compressed regions 14, 15 of the present embodiment is configured by including, as shown in FIG. 3, a plurality of compressed portions 36, 37 which are intermittently and serially provided in the predetermined direction, that is, the longitudinal direction of the deformation guiding portions 11, 12, and are formed by compression, and a plurality of non-compressed portions 38, 39 which are positioned in between the adjacent compressed portions 36, 36, 37, 37 and are not compressed. The compressed portions 36, 37 are the portions in which the thickness is the thinnest in the absorbent body 4 by the compression, the fiber density is the lowest, and are the stiffest.

Incidentally, the relative evaluation with regard to highs and lows of the fiber density and the measurement method of the fiber density are described later.

The compressed portions 36, 37 of the present embodiment are formed by compressing the absorbent core 8 and the core wrapping sheet 9 from the top sheet 2 side (the skin surface side) of the absorbent body 4. Further, in the present embodiment, since the top sheet 2 is not provided with the compressed portions, that is, the compacted portions, in the surface on the top sheet 2 side of the disposable diaper 1, the portion which is recessed toward the non-skin surface side, that is, the back sheet 3 side by the compressed portions 36, 37 is covered by the top sheet 2.

Further, as shown in FIG. 4, the compressed portions 36, 37 are not in contact with the back sheet 3 on the non-skin surface side. This is because, when the absorbent body 4 is compressed, pressure is applied from the skin surface side of the absorbent body 4, whereby the core wrapping sheet which corresponds to the portion connecting the top portion of the protruded portion and the compressed portion is pulled to the compressed portion side, however, when the pressure is removed, the pulled core wrapping sheet tries to return to the top portion side of the protruded portion, and as a result, the compressed portion is pulled to the skin surface side, and the non-skin surface side of the compressed regions 14, 15 in the absorbent body 4 is shifted to the skin surface side. Accordingly, the compressed portions 36, 37 are in a state of being separated from the back sheet 3.

By the compressed portions 36, 37 not being in contact with the back sheet 3 on the non-skin surface side, when the disposable diaper 1 is deformed along the deformation guiding portions 11, 12, the back sheet 3 functions as a buffer to absorb the differences in tensions applied to the skin surface side and to the non-skin surface side of the disposable diaper 1, whereby it is even easier for the disposable diaper 1 to be deformed.

Further, the non-compressed portions 38, 39 are further protruded towards the skin side than the compressed portions 36, 37, however, have protruded heights less than the protruded portions 16 to 19 and are not compressed, whereby have lower fiber density compared to the compressed portions 36, 37, and are the portions which are the softest in the compressed regions 14, 15. Accordingly, when the user touches the deformation guiding portions 11, 12 of the disposable diaper 1 along the longitudinal direction, the texture of the soft non-compressed portions 38, 39 can be felt through the top sheet 2 earlier than that of the compressed portions 36, 37, whereby the feeling is excellent. Further, although depending on the interval of the adjacent compressed portions 36, 36, 37, 37 and each length of the compressed portions 36, 37, the opportunities for the non-compressed portions 38, 39 to be in contact with the skin through the top sheet 2 increase, whereas the opportunities for the compressed portions 36, 37 to be in contact with the skin are suppressed, whereby the compressed portions 36, 37 can be suppressed from being felt with the stiffness thereof. Accordingly, an even softer texture can be obtained.

Further, in the present embodiment, the compressed regions 14, 15 are respectively provided in the central portion in the width direction of the deformation guiding portions 11, 12, and each of the protruded portions 16, 17, 18, 19 is disposed with substantially uniform width on both sides in the longitudinal direction of the compressed regions 14, 15.

The compressed region of the present invention preferably has a width which is ½ or less of the width of the deformation guiding portion. The compressed region of the present invention more preferably has a width which is ¼ or less, and even more preferably has a width which is ⅛ or less, of the width of the deformation guiding portion. By arranging the width of the compressed region to be ½ or less of the width of the deformation guiding portion, even when the user touches the deformation guiding portions 11, 12 of the disposable diaper 1 through the top sheet 2, the opportunities to come in contact with the protruded portions 16, 17, 18, 19 are to be relatively more than the opportunities to come in contact with the compressed region in which stiffness is more easily felt, whereby it is easy for the user to feel the softness of the protruded portion. Further, when the disposable diaper 1 is deformed so as to protrude toward the non-skin surface side, the protruded portions 16, 17 come closer to each other, and the protruded portions 18, 19 come closer to each other, whereby covering the respective compressed regions 14, 15 in which stiffness is increased by compression, and when the skin surface of the user touches the surface of the disposable diaper 1, it is difficult to feel the stiffness of the compressed regions 14, 15 through the top sheet 2. Still further, the lower limit of the ratio of the width of the compressed region with respect to the width of the deformation guiding portion is 1/50, from a manufacturing point of view.

Incidentally, in another embodiment of the present invention, the protruded portions may be disposed with uneven widths in the longitudinal direction of the compressed region.

The width of the deformation guiding portion of the present invention is, for example, 5 to 45 mm, and is preferably 10 to 40 mm, and is more preferably 20 to 30 mm. By arranging the width of the deformation guiding portion to 5 mm or more, when manufacturing the disposable diaper, the possibility that the misalignment of the compressed region with respect to the deformation guiding portion occurs is suppressed, and it is difficult for the formation of the protruded portion to be inhibited. On the other hand, by arranging the width of the deformation guiding portion to 45 mm or less, the possibility that the width of the deformation guiding portion is too wide, the texture through the top sheet 2 is degraded, and the feeling when the absorbent article is worn is deteriorated, can be suppressed.

Further, the width of the compressed region of the present invention is, although depending on the width and the shape of the deformation guiding portion, preferably 0.3 to 8 mm, more preferably 0.4 to 6 mm, and even more preferably 0.5 to 4 mm. By arranging the width of the compressed region to 0.3 mm or more, the possibility that the joining strength by the compression is lowered, and the absorbent core and the core wrapping sheet are peeled off from each other is suppressed, and the deformation which originates at the boundary between the compressed region and the protruded portion can be reliably guided. On the other hand, by arranging the width of the compressed region to 8 mm or less, since when the width of the compressed portion is too wide, it is easier for the stiffness at the compressed portion to be felt directly from above the top sheet or indirectly through the top sheet, the possibility that the texture of the disposable diaper may be deteriorated can be suppressed.

Further, the length of the compressed portion (the size along the longitudinal direction of the compressed region) is, although depending on the length and the shape of the deformation guiding portion, preferably 1 to 20 mm, more preferably 2 to 15 mm, and even more preferably 2.5 to 10 mm. By arranging the length of the compressed portion to 1 mm or more, the possibility that the joining strength by the compression is lowered, and the absorbent core and the core wrapping sheet are peeled off from each other is suppressed, and the deformation which originates at the boundary between the compressed region and the protruded portion can be reliably guided. On the other hand, by arranging the length of the compressed region to 20 mm or less, it is more difficult for the user to feel the portion made to be stiff by compression. Further, the compressed region includes the non-compressed portions which are not compressed and are in a state of being softer than the compressed portions, in between the adjacent compressed portions, whereby the feeling is excellent when the deformation guiding portion of the absorbent article is felt along the longitudinal direction through the top sheet.

On the other hand, the protruded portions 16, 17 (18, 19) of the deformation guiding portion 11 (12) are the portions which are the most protruded toward the skin surface side in the absorbent body 4, and the protruded portions 16, 17 (18, 19) of the respective deformation guiding portion 11 (12) have the substantially same protruded heights. The protruded portions 16 to 19 are the portions which come in contact with the skin earlier than the skin coming in contact with the compressed regions 14, 15, and especially the compressed portions 36, 37 which are stiff and inferior in the texture through the top sheet 2, so as to prevent the skin from feeling the stiffness of the compressed regions 14, 15 as much as possible. Further, since the protruded portions 16, 17 (18, 19) are provided respectively on both sides in the longitudinal direction of the compressed region 14 (15), even when the skin of the user comes in contact with any direction, the user basically feels either one of the protruded portions 16, 17 (18, 19) or both of the protruded portions 16, 17 (18, 19), and when the disposable diaper 1 is deformed so as to protrude toward the non-skin surface side, the protruded portions 16, 17 come closer to each other, and the protruded portions 18, 19 come closer to each other, whereby covering the respective compressed regions 14, 15 in which stiffness is increased by compression. Accordingly, the opportunities for the user to come in contact with the deformation guiding portion 11 (12) through the top sheet 2 are decreased, which makes it difficult to feel the stiffness of the compressed region 14 (15).

As shown in FIG. 4, the protruded portions 16 to 19 of the present embodiment are formed so that the portion on the tip side on the protruded side is substantially semicircular in cross section, and are configured to be soft and capable of coming in contact with the skin with a contact area as narrow as possible. Incidentally, in the present embodiment, the top sheet 2 is disposed so as to be in contact with the portions which are positioned on the most skin surface side of the protruded portions 16 to 19, and when the protruded portions are deformed by an outer force, the top sheet 2 is warped toward the compressed regions 14, 15 side. Accordingly, the protruded heights of the protruded portions 16 to 19 are to be higher by the thickness of the top sheet 2, and the top sheet 2 covers the compressed regions 14, 15, whereby the opportunities for the skin to come in contact with the compressed regions 14, 15, and especially the compressed portions 36, 37 through the top sheet 2 can be even more decreased.

The protruded portions 16 to 19 have a fiber density which is lower than that of the base portions 13.

Accordingly, since the protruded portions 16 to 19 are softer not only than the compressed regions 14, 15 but also than the base portions 13, when the skin touches the protruded portions 16 to 19 through the top sheet 2, a soft texture can be felt. Accordingly, even when the user touches the deformation guiding portions 11, 12 of the disposable diaper 1 through the top sheet 2, it is easy to feel the softness of the protruded portions 16 to 19. Further, when the disposable diaper 1 is deformed so as to protrude toward the non-skin surface side, the protruded portions 16, 17 come closer to each other, and the protruded portions 18, 19 come closer to each other, whereby covering the respective compressed regions 14, 15 in which stiffness is increased by compression, which makes it difficult to feel the stiffness of the compressed region 14 (15) through the top sheet 2 when the skin surface of the user touches the surface of the disposable diaper 1. As a result, an excellent feeling when being worn can be obtained by the disposable diaper 1 as a whole.

In the present invention, the fiber density of the protruded portions has only to be lower than the fiber density of the base portions, however, the fiber density of the protruded portions is, preferably within the range of 0.20 to 0.80 times as much as, more preferably within the range of 0.25 to 0.75 times as much as, and even more preferably within the range of 0.30 to 0.70 times as much as, the range of the fiber density of the base portions. The fiber density of the protruded portions is 0.20 times as much as the range of the fiber density of the base portions or more, from a manufacturing point of view. On the other hand, when the fiber density of the protruded portions is 0.80 times as much as the range of the fiber density of the base portions or less, the user can reliably feel the relative softness of the protruded portions with respect to that of the base portions.

Further, in the present invention, the height of each of the protruded portions (the distance (thickness) between the portion which is positioned on the most skin surface side in the protruded portion (the top portion) and the non-skin surface side of the absorbent body) is preferably approximately 1.2 to 3 times as much as, and more preferably 1.3 to 2.5 times as much as, and even more preferably 1.5 to 2 times as much as, the thickness of each of the base portions (except the recessed portions). When the height of each of the protruded portions is 1.2 times as much as the thickness of each of the base portions or more, when the absorbent article is deformed so as to protrude toward the non-skin surface side, the protruded portions come closer to each other, and more reliably cover the compressed region which is positioned between the protruded portions, whereby it is difficult for the stiffness at the compressed portion to be felt by the user directly from above the top sheet or through the top sheet. On the other hand, when the height of each of the protruded portions is 3 times as much as the thickness of each of the base portions or less, when the absorbent body is deformed, the inhabitation of the bending due to the interference between the protruded portions can be suppressed, so that the deformation guiding function of the deformation guiding portions can be fully demonstrated, and further, the disposable diaper 1 as a product can be easily folded to be housed in a package.

Incidentally, the measurement method of the thickness of the portions which configure the absorbent article is explained in the description of the measurement method of the fiber density, which is described later.

By the way, as described above, the absorbent body 4 of the present embodiment includes the absorbent polymers 8b, however, the basis weight of the absorbent polymers 8b included in the deformation guiding portions 11, 12 is less than the basis weight of the absorbent polymers 8b included in the base portions 13.

In this manner, since the basis weight of the absorbent polymers 8b included in the deformation guiding portions 11, 12 is less than that in the base portions 13, when the absorbent body 4 absorbs liquid excrement, the expansion of the deformation guiding portions 11, 12 due to the swelling of the absorbent polymers 8b is smaller than that of the base portions 13. Accordingly, it is difficult for the deformation of the disposable diaper 1 which originates at the boundary between the deformation guiding portions 11, 12, especially the compressed regions 14, 15 and the protruded portions 16 to 19 to be inhibited, whereby the deformed state of the disposable diaper 1 can be stably maintained even after the absorbent body 4 absorbed liquid excrement, and the comfortable feeling can be maintained. Further, when the absorbent polymers 8b are present in a large amount at the compressed positions, such as the compressed portions 36, 37, etc., of the compressed regions 14, 15 or in the vicinity thereof, it is easier for the absorbent polymers 8b to be exposed to the skin surface side when being compressed, whereby the texture of the absorbent body 4 may be degraded, however, by making the basis weight of the absorbent polymers 8b included in the deformation guiding portions 11, 12 less than that in the base portions 13, it is difficult for these problems to occur and the degrading of the texture can be suppressed.

The basis weight of the absorbent polymers included in the deformation guiding portions is preferably less than 80 mass % the basis weight of the absorbent polymers included in the base portions. When the basis weight of the absorbent polymers included in the deformation guiding portions is 80 mass % of the basis weight of the absorbent polymers included in the base portions or more, as described above, it is easier for the absorbent polymers to be exposed to the skin surface side when being compressed, whereby the texture may be degraded. The lower limit is not particularly limited, however, in a case in which the absorbent polymers are included in the deformation guiding portion, the absorption capacity in the deformation guiding portions can be fully secured, and accordingly, it is preferable that the basis weight of the absorbent polymers included in the deformation guiding portions is 25 mass % of the basis weight of the absorbent polymers included in the base portions or more. Incidentally, in the present invention, the absorbent polymers may not be included in the deformation guiding portions.

Further, the mass inclusion ratio, with respect to the absorbent body 4, of the absorbent polymers 8b included in the portion which extends in the thickness direction T on the non-skin surface side of the recessed portions 22 in each of the base portions 13 is more than the mass inclusion ratio, with respect to the absorbent body 4, of the absorbent polymers 8b included in the portion other than the portion which extends in the thickness direction T on the non-skin surface side of the recessed portions 22 in each of the base portions 13 (that is, the flat portion 21).

Accordingly, the portion which extends in the thickness direction T on the non-skin surface side of the recessed portions 22 in each of the base portions 13 has room for expansion as much as the recessed amount toward the non-skin surface side of the recessed portions 22, whereby even when the absorbent polymers 8b included in the portion which extends in the thickness direction T on the non-skin surface side of the recessed portions 22 are swollen, it is difficult for the user to be inhibited from feeling the softness of the protruded portions 16 to 19. Further, the absorbability in the vicinity of the protruded portions 16 to 19 in which the mass inclusion ratio of the absorbent polymers 8b included therein is less than that included in the base portions 13, can be stably secured.

Incidentally, "a mass inclusion ratio (%) of absorbent polymers" in the present description means the mass ratio of absorbent polymers with respect to the total mass of the water absorbent fiber and the absorbent polymers included in an absorbent body.

Further, the mass inclusion ratio (%) of absorbent polymers in the present description is measured as follows.

1. Calculation of Water Retention Ratio of the Water Absorbent Fiber and the Absorbent Polymers
(1) The measurement object portion of the absorbent body is cut out.
(2) The cut out sample is immersed in a toluene solution, and the core wrapping sheet is removed, so as to obtain sample A which includes the water absorbent fiber and the absorbent polymers only.
(3) The sample A is dried in an oven at 80° C. for 12 hours or more, and the sample A which is in an absolutely dry state is stored in a mesh of about a size from which the water absorbent fiber and the absorbent polymers do not drop out.
(4) The mass of the sample A stored in the mesh is measured, and the mass of the mesh itself in an absolutely dry state which is measured in advance (the dry mass of the mesh) is subtracted therefrom, so as to obtain the dry mass Wd (g) of the sample A.
(5) The sample A stored in the mesh is immersed in an ion exchanged water for 60 minutes, and dehydration by a centrifugal dehydrator is performed with a centrifugal force of 150 G for 2 minutes.
(6) The total mass of the sample A after dehydration and the mesh is measured, and the dry mass of the mesh is subtracted from the total mass, so as to obtain the total water retention amount Ws (g) of the sample A and the mesh.
(7) Each step of the immersion, the dehydration, and the mass measurement as described in 1. (5) to (6) is performed only for the mesh, and the water retention amount Wm (g) of the mesh itself is calculated.
(8) The water retention ratio Hall of the sample A only (the water absorbent fiber and the absorbent polymers) is calculated by the following calculation formula.

[Formula 1]

$$\text{Hall} = \frac{Ws - Wm}{Wd} \times 100 \qquad (1)$$

2. Calculation of the Water Retention Ratio of the Water Absorbent Fiber Only
(1) The measurement object portion of the same absorbent body is cut out, and the water absorbent fiber only is removed from the cut out sample, so as to obtain sample B.
(2) The water retention ratio Hp of the water absorbent fiber is calculated by the same steps described in the above mentioned 1. (3) to (8) for the sample B.

3. Calculation of the Water Retention Ratio of the Absorbent Polymers Only
(1) The measurement object portion of the same absorbent body is cut out, and the absorbent polymers only are removed from the cut out sample, so as to obtain sample C.
(2) The water retention ratio Hsap of the absorbent polymers is calculated by the same steps described in the above mentioned 1. (3) to (8) for the sample C.

4. Calculation of the Ratio of (the Mass of the Absorbent Polymers)/(the Mass of the Water Absorbent Fiber+the Absorbent Polymers)
(1) In accordance with the following procedure, a calibration curve is prepared with the horizontal axis as the water retention ratio and the vertical axis as the mass inclusion ratio of the absorbent polymers.
(2) The value calculated in the above mentioned 2. is taken as the case in which the absorbent polymer ratio is 0%, and (Hp, 0) is plotted on a graph.

(3) The value calculated in the above mentioned 3. is taken as the case in which the absorbent polymer ratio is 100%, and (Hsap, 100) is plotted on a graph.
(4) The two points plotted in the above mentioned 4. (2) and (3) are connected, and a calibration curve ($Y=aX+b$) represented by a linear function is created.
(5) The Hall calculated in the above mentioned 1. (8) is substituted for X of the calibration curve, and the mass inclusion ratio Y (%) of the absorbent polymers in the measurement object portion is calculated.

The mass inclusion ratio of the absorbent polymers included in the portion which extends in the thickness direction on the non-skin surface side of the recessed portions in each of the base portions is preferably 105% to 150% of the mass inclusion ratio of the absorbent polymers included in the portion other than the portion which extends in the thickness direction on the non-skin surface side of the recessed portions in each of the base portions.

When the mass inclusion ratio of the absorbent polymers included in the portion which extends in the thickness direction on the non-skin surface side of the recessed portions in each of the base portions is 105% of the mass inclusion ratio of the absorbent polymers included in the portion other than the portion which extends in the thickness direction on the non-skin surface side of the recessed portions in each of the base portions, or more, the absorbability by the absorbent polymers in the absorbent body can be stably secured, and further, in the manufacturing steps of the absorbent body which are described later, it is easier for the recessed portions 22 to be formed, whereby the recessed portions themselves are to be the portion at which the bending of the absorbent article originates, and the absorbent article can be more stably deformed. On the other hand, when the mass inclusion ratio of the absorbent polymers included in the portion which extends in the thickness direction on the non-skin surface side of the recessed portions in each of the base portions is 150% of the mass inclusion ratio of the absorbent polymers included in the portion other than the portion which extends in the thickness direction on the non-skin surface side of the recessed portions in each of the base portions, or less, it is difficult for the absorbent polymers to be stuck from each other, and the absorbability of the absorbent body can be secured, as well as it being difficult for the absorbent polymers to be exposed to the skin surface side, so as to achieve soft texture.

Incidentally, in the present description, the evaluation with regard to highs and lows of the fiber density and the measurement method of the fiber density are as follows. Incidentally, the measurement method of the thickness of a sample which includes the measurement object portion is also explained in the steps of the measurement method of the fiber density.

1. Obtainment of an X-Ray CT Image of a Sample
(1) A sample D which includes the measurement object portion is prepared from the absorbent article. The sample D is an absorbent body which includes the absorbent core and the core wrapping sheet, being removed of the elastic members, the top sheet, and the back sheet, etc., from the absorbent article, and is also a specimen for an X-ray CT observation which is cut out into a size of 20×20 mm in a plan view.

Incidentally, in a case in which the absorbent article is integrally formed by the absorbent body, the top sheet, and the back sheet, and the top sheet and the back sheet cannot be removed without destroying the shape of the absorbent body, the sample D is a specimen for an X-ray CT observation which includes the absorbent body having the absorbent core and the core wrapping sheet, being removed of the elastic members from the absorbent article, and further including the top sheet and the back sheet, and is cut out into a size of 20×20 mm in a plan view.
(2) The following X-ray CT apparatus and the image processing software are used, and the above mentioned sample D is tomographically photographed, whereby an internal cross section photograph including the thickness direction thereof is obtained in a BMP format.

Measurement and Photographing Device 3D measurement X-ray CT apparatus: TDM-1000-IS/SP (manufactured by Yamato Scientific Co., Ltd.)

3D volume rendering software (image processing software): VG-Studio MAX (manufactured by Nihon Visual Science, Inc.)

Measurement and Photographing conditions: 30 kv of tube voltage, 30 µA of tube current, and 1024 pixel×1024 pixel of pixel numbers Incidentally, the visual field size is set to be the maximum magnification in the range in which the outer periphery of the specimen for observation is contained.

2. Evaluation of Highs and Lows of the Fiber Density

When comparing the relative highs and lows of the fiber density in different portions in the absorbent body (for example, comparing the base portion except for the recessed portion and the protruded portion), the internal cross section photographs (an XY cross section, a YZ cross section, and a ZX cross section) in the BMP format including the portions are obtained by the method of the above mentioned 1. (1), and the relative comparison of the fiber density is judged by visual observation.

3. Measurement Method of the Thickness of the Measurement Object Portion in the Sample The YZ cross section or the ZX cross section, among the internal cross section photograph in the BMP format obtained by the above mentioned 1. (1), is analyzed by using an image analyzing software USB digital scale manufactured by Scala, Inc., and the thickness (the length in the Z direction) of the measurement object portion in the sample is calculated. Incidentally, when calculating the thickness of the measurement object portion in the sample, it is preferable that samples are cut out from five or more different portions including the portion, the internal cross section photographs in the BMP format are obtained, the thickness in the portion in each of the samples is calculated by the same procedures, and the average value thereof is regarded as the thickness of the measurement object portion.

4. Calculation of the Fiber Density
(1) A sample E is cut out from the sample D which has been used for the X-ray CT photography so that only the measurement object portion is contained.
(2) The internal cross section photograph in the BMP format is obtained also for sample E in the same manner as 1. (1), the XY cross section thereof is analyzed by using the image analyzing software USB digital scale manufactured by Scala, Inc., the length in the X direction and the length in the Y direction of the measurement object portion in the sample E are obtained, and the product of the lengths thereof is calculated, whereby the cross sectional area of the sample E in a plan view is calculated.
(3) The total mass of the cut out sample E is measured by using an electronic balance (GR-300 manufactured by A&D Company, Limited, with accuracy: to four decimal places), and then the members (such as the top sheet, the core wrapping sheet, etc.) other than the absorbent core included in the sample E are removed so as to calculated the mass We.

(4) In accordance with the calculation method of the ratio of the above mentioned mass of the absorbent polymers/(the mass of the water absorbent fiber+the absorbent polymers), the ratio of the water absorbent fiber (100-Y) (%) is calculated from the ratio of the absorbent polymers Y (%), to be multiplied by the mass We, whereby the mass of the water absorbent fiber is calculated.

(5) The obtained mass of the water absorbent fiber is divided by the value of the product of the thickness obtained at 3. and the cross sectional area obtained at 4. (2), whereby the fiber density is calculated.

The following method may be used when manufacturing the disposable diaper 1 which has the above mentioned configuration.

Incidentally, in the present description, "a direction which is parallel to the conveying direction of a material or a product" is referred to as "an MD direction", "a direction which is orthogonal to the MD direction on a horizontal plane" (that is, the width direction of the production line) is referred to as "a CD direction", and "a direction which is orthogonal to the MD direction and to the CD direction" (that is, the vertical direction of the production line) is referred to as "a TD direction".

FIG. 5 shows one example of a manufacturing apparatus to manufacture the disposable diaper 1 according to the first embodiment. The manufacturing apparatus 50 includes a conveying tube 51 which conveys the absorbent material including the opened water absorbent fibers 8a and the absorbent polymers 8b, and a freely rotatable suction drum 52 which sucks the absorbent material inside the conveying tube 51 and laminates the sucked absorbent material in a plurality of recessed molding members 53 which are disposed at a constant interval along the circumferential direction of the outer circumferential surface, whereby forms a first laminated body 61 which is to be the absorbent core 8 of the absorbent body 4 in a later process.

Further, the manufacturing apparatus 50 includes an unwinding roll 54 for the core wrapping sheet continuous body which places the first laminated body 61 at the outer circumferential surface of the suction drum 52, unwinds the longitudinal core wrapping sheet continuous body 62 which is to cover the first laminated body 61, and covers the first laminated body 61 with the core wrapping sheet continuous body 62, whereby forms a second laminated body 63.

Further, the manufacturing apparatus 50 includes a pressing device 55 including a pair of upper and lower (TD direction) press rolls 55a, 55b which apply pressure in the thickness direction to compress the second laminated body 63, and a compressing device 56 which is positioned downstream in the conveying direction MD of the pressing device 55 and compresses the predetermined position of the third laminated body 64 (64a, 64b) formed by being compressed in the thickness direction by the pressing device 55 to perform an embossing treatment.

The compressing device 56 forms the compressed regions 14, 15 of the deformation guiding portions 11, 12, and includes a pair of upper and lower (TD direction) rolls 56a, 56b, in which one roll 56a (in this case, the upper side roll) is configured to be an embossing roll to compress the third laminated body 64 in the thickness direction, which includes a plurality of embossing pins on an outer circumferential surface disposed in accordance with the shape and the position of the compressed portions 36, 37 of the compressed regions 14, 15. Incidentally, the other roll 56b (in this case, the lower side roll) is configured to be an anvil roll in which the outer circumferential surface is flat.

Further, the manufacturing apparatus 50 includes, at the further downstream in the conveying direction MD than the compressing device 56, an unwinding roll 57 for the top sheet continuous body which unwinds and laminates the longitudinal top sheet continuous body 66 which is to be the top sheet 2 with respect to one surface (in the case of FIG. 5, the upper surface) of the fourth laminated body 65 which has been subjected to the embossing treatment.

Further, the manufacturing apparatus 50 includes an unwinding roll 58 for the back sheet continuous body which unwinds and joins the longitudinal back sheet continuous body 68 which is to be the back sheet 3 with respect to the surface (in the case of FIG. 5, the lower surface) on the opposite side of the top sheet continuous body 66 in the fifth laminated body 67 which is formed by laminating the top sheet continuous body 66 to the fourth laminated body 65, so as to form the sixth laminated body 69.

Incidentally, at the further downstream in the conveying direction MD than the unwinding roll 58 for the back sheet continuous body, a cutting device (which is not shown) which cuts the laminated body 69 into the shape of the disposable diaper 1 as a product, so as to obtain a single disposable diaper 1, and each device (which is not shown) which attaches the side sheets 5, 5 and the tape fastener 6 to the sixth laminated body 69 is provided, however, since these devices are normal devices known in the art, the detailed description thereof is omitted.

When manufacturing the disposable diaper 1 by using the above mentioned manufacturing apparatus 50, basically, a first step of forming the first laminated body 61, a second step of covering the first laminated body 61 with the core wrapping sheet continuous body 62 so as to obtain the second laminated body 63, a third step of compressing the second laminated body 63 in the thickness direction by the pressing device 55 so as to obtain the third laminated body 64, and a fourth step of compressing the predetermined position of the third laminated body 64 by the compressing device 56, whereby performing the embossing treatment so as to obtain the fourth laminated body 65, are sequentially performed. Further, a fifth step of laminating the top sheet continuous body 66 onto the fourth laminated body 65 so as to obtain the fifth laminated body 67, and a sixth step of joining the back sheet continuous body 68 to the fifth laminated body 67 so as to obtain the sixth laminated body 69, are sequentially performed.

First, the first step of forming the first laminated body 61 which is to finally configure the absorbent core 8 of the absorbent body 4.

In the first step, the absorbent material including the water absorbent fibers 8a and the absorbent polymers 8b is sucked by the suction drum 52 through the conveying tube 51, and is laminated inside the molding member 53 on the outer circumferential surface of the suction drum 52, so as to form the first laminated body 61.

Figure 6A:
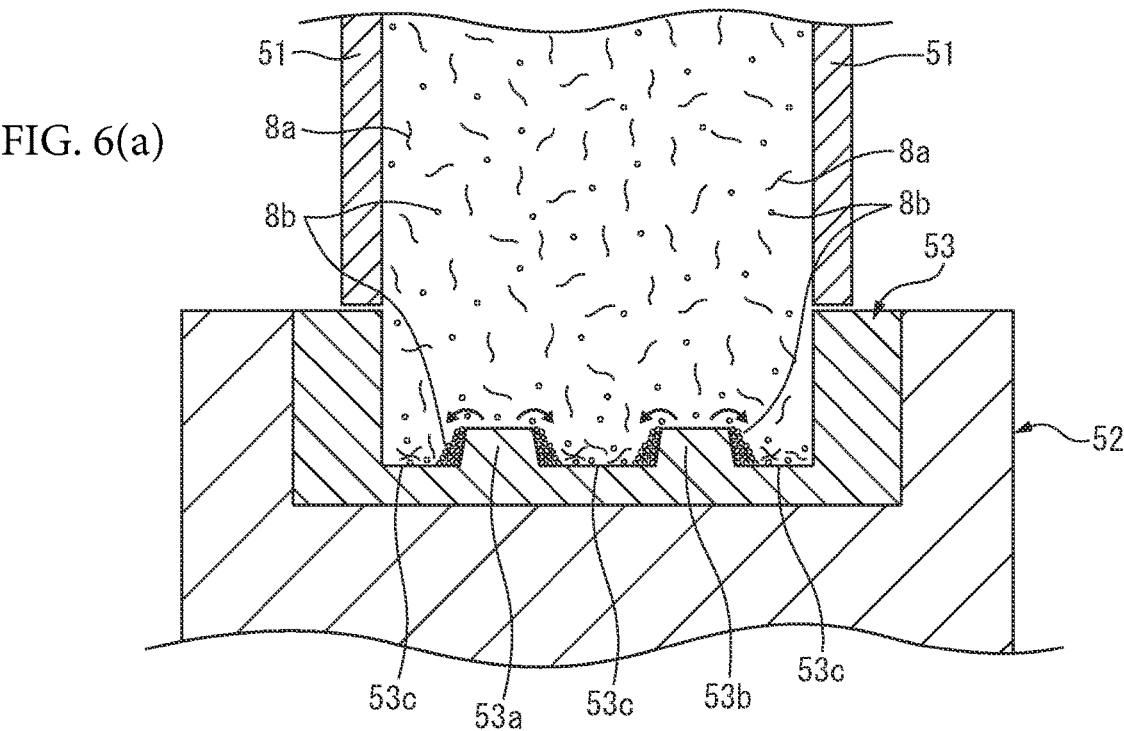
FIG. 6(a) is a main portion enlarged end view which schematically shows a state in which an absorbent material is supplied inside a molding member which is provided at an outer circumferential surface of a suction drum that configures the manufacturing apparatus of FIG. 5.
Figure 6B:
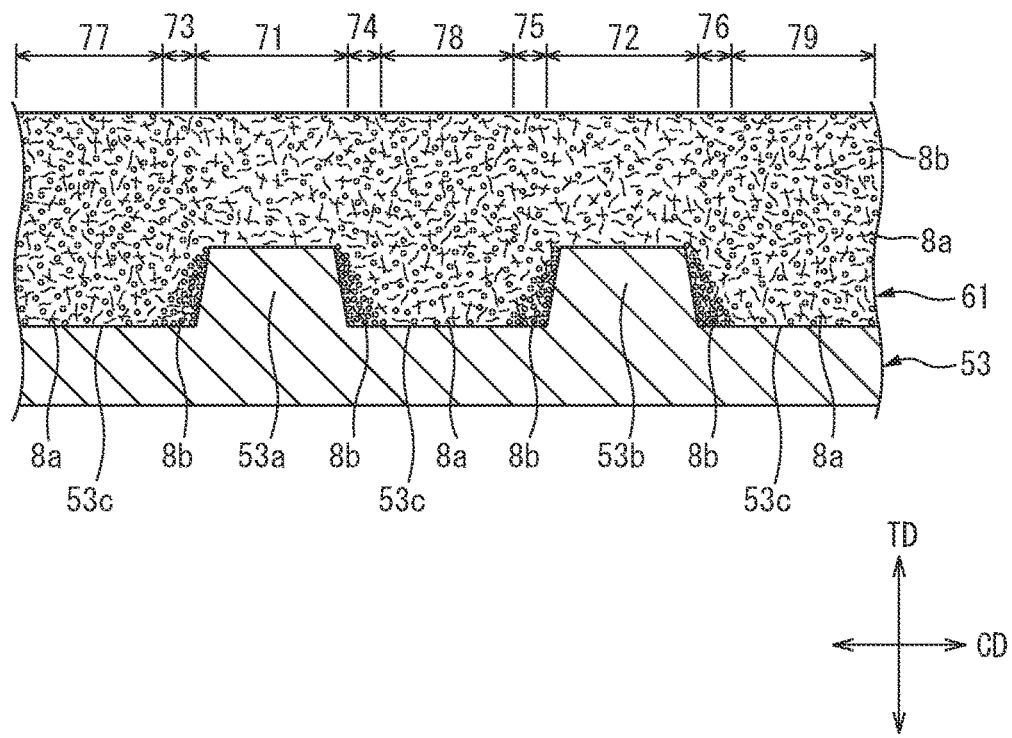
FIG. 6(b) is a main portion enlarged end view of a first laminated body which is laminated inside the molding member.

At this time, as shown in FIG. 6(a), the absorbent material is supplied from above to the inside of the molding member 53, and the molding member 53 includes, at the bottom portion thereof, a pair of protrusions 53a, 53b having a rectangular cross section which extend in the circumferential direction of the suction drum 52. To be more specific, each of the protrusions 53a, 53b has a trapezoidal shape cross section in which an upper base (the side to which the absorbent materials 8a, 8b are supplied) is short, and the lower base is long, that is, tapered as it approaches the tip. Further, when manufacturing the disposable diaper 1, as shown in FIG. 6(b), the side surface of each of the protrusions 53a, 53b has a configuration of having a relatively steep slope. The pair of protrusions 53a, 53b are disposed, at positions adapted to the positions of the pair of deformation guiding portions 11, 12 of the absorbent body 4, so as to have the shape and the width in the longitudinal direction adapted to the shape and the width in the longitudinal direction of the pair of deformation guiding portions 11, 12. Further, the molding member 53 includes a plurality (in the present embodiment, three pairs disposed in parallel in the circumferential direction of the suction drum 52) of protrusions for forming the notch portions (which are not shown) which protrude from the bottom portion toward the upper side in the TD direction in FIG. 5 and extend from the both end portions in the CD direction toward the respective central portion side in the CD direction.

Further, when the absorbent material is supplied to the inside of the molding member 53, since the water absorbent fibers 8a are light and soft, it is difficult for the water absorbent fibers 8a to be bounced back even when collided with the pair of protrusions 53a, 53b, whereby is accumulated approximately evenly inside the molding member 53.

On the other hand, the absorbent polymers 8b, at the stage when the absorbent material begins to be supplied to the inside of the molding member 53, collide with the tip surface of the protrusions 53a, 53b, bounce back and move without staying at the collided position, and finally reach the portion other than the protrusions 53a, 53b in the bottom portion 53c to be accumulated. This is because, in addition to the fact that the absorbent polymers 8b are normally granular, the mass per one absorbent polymer is relatively large, and it is easy for the absorbent polymers 8b to be influenced by their own kinetic energy also due to the suction of the suction drum 52, whereby it is easy for the absorbent polymers 8b to be bounced back when collided with the tip surface of the pair of protrusions 53a, 53b, and is difficult for the absorbent polymers 8b to stay at the collided position.

Incidentally, after a while from the beginning of the supply of the absorbent material to the inside of the molding member 53, since the water absorbent fibers 8a are accumulated also on the protrusions 53a, 53b and even when the absorbent polymers 8b collides therewith, the impact is absorbed by the softness of the water absorbent fibers 8a, it is difficult for the absorbent polymers 8b to be bounced back. As a result, the absorbent material is finally to be accumulated approximately evenly inside the molding member 53.

Accordingly, as shown in FIG. 6(b), in the width direction of the first laminated body 61, a plurality of portions at which the mass inclusion ratio (%) of the absorbent polymers 8b with respect to the absorbent body 4 is different are to be present.

That is, at the portions corresponding to just above the pair of protrusions 53a, 53b inside the molding member 53, the inclusion ratio of the absorbent polymers is the lowest by the movement of the absorbent polymers 8b, whereby are the low inclusion ratio regions 71, 72. On the other hand, at the portions along the side wall portions of the pair of protrusions 53a, 53b and the vicinity thereof, the inclusion ratio of the absorbent polymers is the highest due to the presence of the absorbent polymers 8b which has moved thereto, whereby are the high inclusion ratio regions 73 to 76. Further, at the portions in which the absorbent polymers 8b are not influenced by the pair of protrusions 53a, 53b inside the molding member 53, the absorbent polymers 8b are evenly accumulated, whereby have a normal amount of inclusion ratio, that is, are the medium inclusion ratio regions 77 to 79 in which the inclusion ratio is lower than that in the high inclusion ratio regions 73 to 76 and is higher than that in the low inclusion ratio regions 71, 72.

To be more specific, from one side to the other side in the width direction inside the molding member 53 (from left to right in FIG. 6(b)), the medium inclusion ratio region 77, the high inclusion ratio region 73, the low inclusion ratio region 71, the high inclusion ratio region 74, the medium inclusion ratio region 78, the high inclusion ratio region 75, the low inclusion ratio region 72, the high inclusion ratio region 76, and the medium inclusion ratio region 79 of the absorbent polymers are aligned in this order. Especially, the low inclusion ratio regions 71 (72) of the absorbent polymers are in a state of being positioned between the two high inclusion ratio regions 73, 74 (75, 76).

Incidentally, the first laminated body 61 includes three pairs of notch portions (which are not shown) at which portions of the edge portion on both end portions in the width direction are cut out, and are formed by the above mentioned protrusions for forming the notch portion.

After the first step, the second step is performed, in which the first laminated body 61 inside the molding member 53 is placed on the core wrapping sheet continuous body 62 with an adhesive agent such as a hot melt type adhesive agent, etc., applied in between, by the rotation of the suction drum 52, and the outer circumferential surface of the first laminated body 61 is covered with the core wrapping sheet continuous body 62, whereby the second laminated body 63 is obtained.

In the second step, first, the rotating suction drum 52 transfers and places the first laminated body 61 inside the molding member 53 on the core wrapping sheet continuous body 62 which is unwound from the unwinding roll 54 for the core wrapping sheet continuous body and moves in the conveying direction MD. Further, by the bending means which is not shown, the core wrapping sheet continuous body 62 is bent in the width direction CD which is orthogonal to the conveying direction MD, along the outer circumferential surface of the first laminated body 61, and the core wrapping sheet continuous body 62 is wound around the first laminated body 61 to cover the first laminated body 61, whereby the longitudinal second laminated body 63 is obtained.

After the second step, the third step is performed, in which the second laminated body 63 is compressed in the thickness direction, whereby third laminated body 64 is obtained.

Figure 7A:
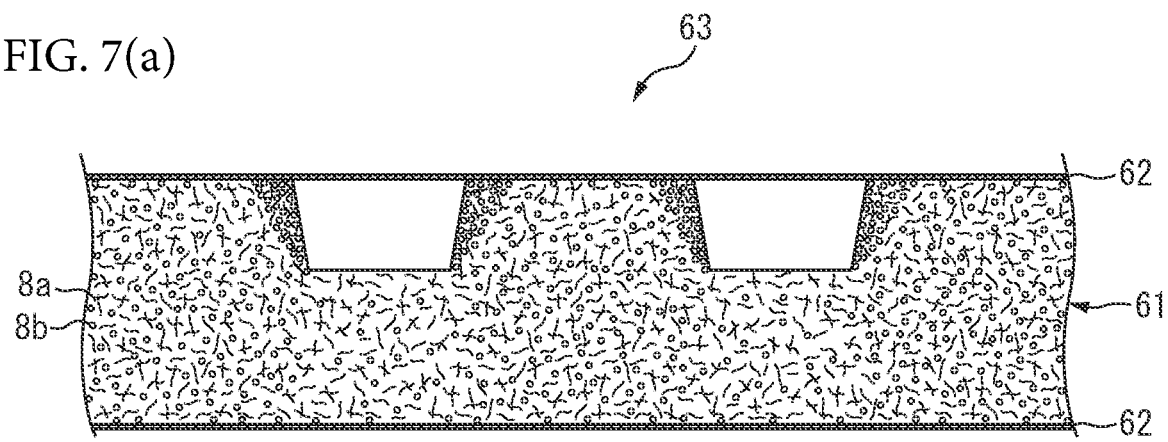
FIG. 7(a) is a main portion enlarged end view of a second laminated body.
Figure 7B:
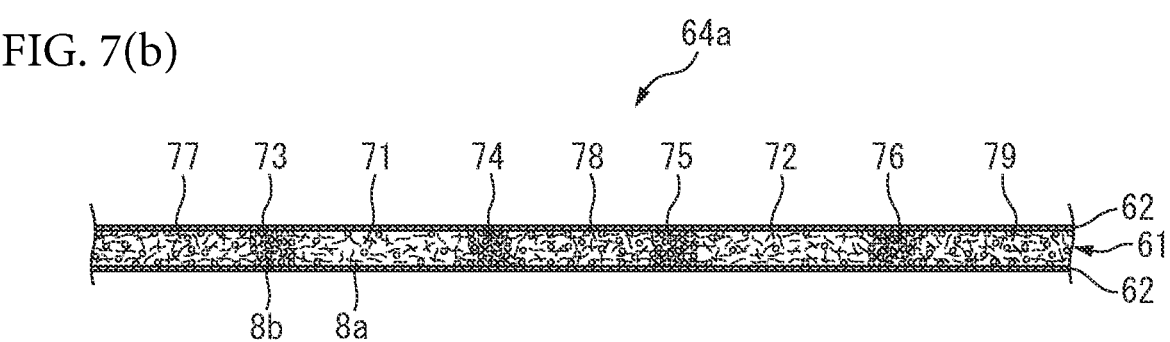
FIG. 7(b) is a main portion enlarged end view of a third laminated body in a state immediately after being compressed in a third step.

In the third step, by passing the second laminated body 63 through between the pair of press rolls 55a, 55b of the pressing device 55, the second laminated body 63 as shown in FIG. 7(a) is compressed in the thickness direction TD. At this time, as shown in FIG. 7(b), the portions at which the mass inclusion ratio of the absorbent polymers with respect to the width direction is different in the first laminated body 61 are compressed in the thickness direction TD as they are, and the third laminated body 64a is formed in which the state of the mass inclusion ratio of the absorbent polymers in the width direction of the first laminated body 61 being different is maintained.

In the third laminated body 64a, since the absorbent polymers 8b move into the gaps between the surrounding water absorbent fibers 8a when being compressed, the absorbent polymers 8b tend to be compacted by the pressure applied from the pressing device 55 at the portions in which the absorbent polymers 8b are present in the second laminated body 63 (and to be more specific, the first laminated body 61).

Further, the state in which the thickness of the third laminated body 64a, which is the second laminated body 63 immediately after passing through the pressing device 55, has recovered to some extent, is to be the third laminated body 64*b*.

Figure 7C:
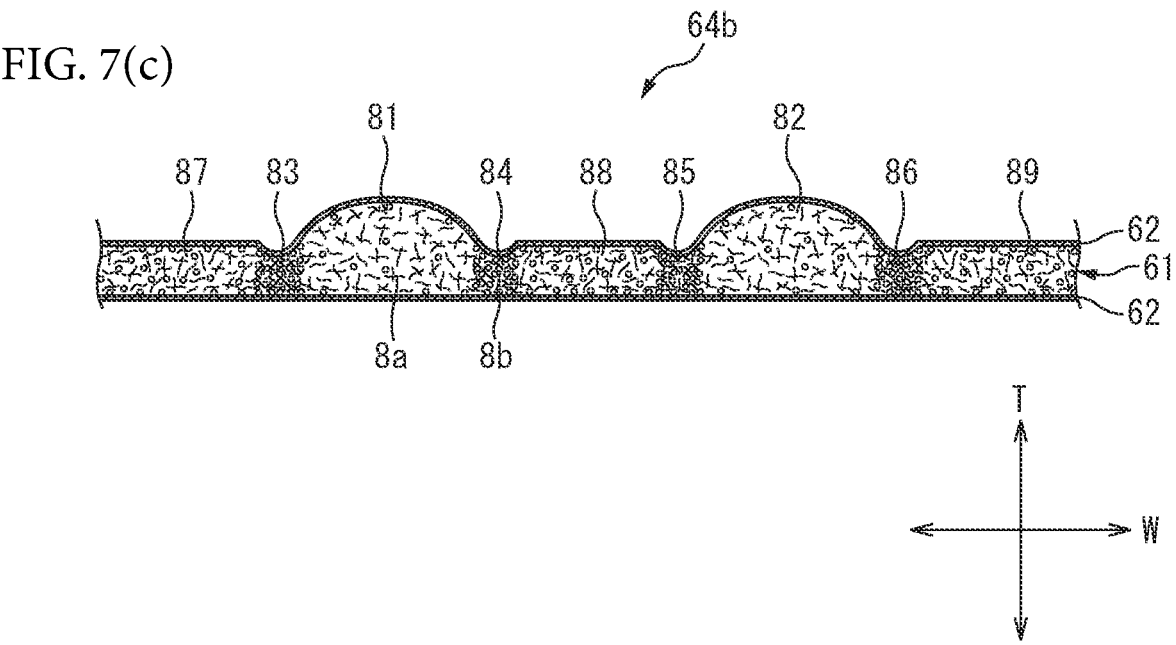
FIG. 7(c) is a main portion enlarged end view of third laminated body before being compressed in a fourth step, which are formed in the manufacturing method of the absorbent article of the first embodiment according to the present invention.

That is, the thickness of the second laminated body 63 is recovered to some extent after passing through the pressing device 55, with the help of the softness of the water absorbent fibers 8*a*, however, as shown in FIG. 7(*b*), at the high inclusion ratio regions 73 to 76 of the absorbent polymers, since the amount of the absorbent polymers 8*b* which move into the gap between the water absorbent fibers 8*a* is large, such regions are compacted by being applied with pressure and it is difficult to recover the thickness thereof. Further, at the medium inclusion ratio regions 77 to 79 of the absorbent polymers, since the amount of the absorbent polymers 8*b* which move into the gap between the water absorbent fibers 8*a* is less than that in the high inclusion ratio regions 73 to 76, the thickness is more recovered compared to the high inclusion ratio regions 73 to 76. Further, at the low inclusion ratio regions 71, 72 of the absorbent polymers, since the amount of the absorbent polymers 8*b* which move into the gap between the water absorbent fibers 8*a* is extremely small, and conversely the amount of the soft water absorbent fibers 8*a* is large, such regions are not very much compacted even being applied with pressure, and the thickness thereof is greatly recovered compared to the medium inclusion ratio regions 77 to 79.

As a result, as shown in FIG. 7(*c*), the thickness does not recover at the high inclusion ratio regions 73 to 76 of the absorbent polymers, to form the portions 83 to 86 which correspond to the recessed portions 22 of the base portions 13 of the absorbent body 4. Since there are four high inclusion ratio regions of the absorbent polymers, four portions are formed which correspond to the recessed portions 22. Further, the low inclusion ratio regions 71, 72 which are adjacent to the high inclusion ratio regions 73 to 76 of the absorbent polymers recover the thickness in the direction toward the top sheet side which is softer compared to the back sheet side and is easier to be deformed, that is, toward the upper surface side, so as to form the protruded portions 81, 82 which protrude gently toward the upper surface side. The protruded portions 81, 82 as a whole are to correspond to the portions of the deformation guiding portions 11, 12. Incidentally, since there are two low inclusion ratio regions of the absorbent polymers, two protruded portions are formed. Further, the medium inclusion ratio regions 77 to 79 of the absorbent polymers recover the thickness thereof to some extent, and are to be the portions 87 to 89 which correspond to the portions other than the recessed portions 22 of the base portions 13 of the absorbent body 4. Since there are three medium inclusion ratio regions of the absorbent polymers, three portions which correspond to the portions other than the recessed portions in the base portions 13 are formed.

Finally, the state in which the portions 83 to 86 which correspond to the recessed portions of the base portions of the absorbent body, the protruded portions 81, 82, and the portions 87 to 89 which correspond to the portions other than the recessed portions in the base portions are formed is the third laminated body 64*b*.

After the third step, the fourth step is performed, in which the predetermined position of the third laminated body 64*b*, and to be more specific, the protruded portions 81, 82 of the third laminated body 64*b* are compressed by the compressing device 56, whereby performing the embossing treatment so as to obtain the fourth laminated body 65.

In the fourth step, the third laminated body 64*b* passes through the pair of upper and lower rolls 56*a*, 56*b* of the compressing device 56, whereby the protruded portions 81, 82 of the third laminated body 64*b* is compressed in the thickness direction TD. At this time, the embossing pins of the embossing roll, which is the upper side roll 56*a*, of the compressing device 56 sequentially compresses the protruded portions 81, 82 of the third laminated body 64*b* in the thickness direction TD. The compressed portions in the protruded portions 81, 82 are to be the portions which correspond to the compressed regions 14, 15 of the absorbent body 4, and to be more specific, correspond to the compressed portions 36, 37. Further, the both side portions in the longitudinal direction of the compressed portions in the protruded portions 81, 82 are not compressed, so as to be the portions which correspond to the protruded portions 16 to 19 of the absorbent body 4.

Accordingly, the fourth laminated body 65 is formed.

After the fourth step, the fifth step is performed, in which the top sheet continuous body 66 which is unwound from the unwinding roll 57 for the top sheet continuous body is laminated on the upper surface of the fourth laminated body 65, with an adhesive agent such as a hot melt type adhesive agent, etc., applied in between so as to obtain the longitudinal fifth laminated body 67.

Further, after the fifth step, the sixth step is performed, in which the back sheet continuous body 68 which is unwound from the unwinding roll 58 for the back sheet continuous body is joined to the lower surface of the fifth laminated body 67, with an adhesive agent such as a hot melt type adhesive agent, etc., applied in between so as to obtain the longitudinal sixth laminated body 69. Incidentally, the cross section (end face) shape of the sixth laminated body 69 which is formed by the sixth step is substantially the same as the shape shown in FIG. 4.

After the sixth step, the sixth laminated body 69 is cut into the shape of the disposable diaper 1 by a cutting device.

As a result, the disposable diaper 1 is completed in which the absorbent body 4 includes the deformation guiding portions 11, 12 and the base portions 13 which are disposed on both sides of the deformation guiding portions 11, 12, and the deformation guiding portions 11, 12 include the compressed regions 14, 15 and the protruded portions 16, 17, 18, 19 which are disposed on both sides of the compressed regions 14, 15.

According to the disposable diaper 1 which has the above mentioned configuration, the boundary portion between the compressed regions 14, 15 and the protruded portions 16 to 19 of the deformation guiding portions 11, 12 is to be a portion at which the bending originates due to the rigidity differences, whereby makes it possible to stably guide the deformation of the absorbent body 4, and the disposable diaper 1 as a whole, in accordance with the three dimensional shape of the body of the user. Further, since the protruded portions 16, 17, 18, 19 are provided on both sides in the direction in which the compressed regions 14, 15 of the deformation guiding portions 11, 12 extend, so as to protrude toward the skin surface side, in which the fiber density is lower than that in the base portions 13 and are relatively soft, even when the user touches the deformation guiding portions 11, 12 through the top sheet 2, it is easy for the user to feel the softness of the protruded portions 16, 17, 18, 19. Further, when the disposable diaper 1 is deformed so as to protrude toward the non-skin surface side, the protruded portions 16, 17 come closer to each other and the protruded portions 18, 19 come closer to each other, so as to cover the compressed regions 14, 15 in which the stiffness is increased by compression, whereby the skin surface of the user comes in contact with the surface of the disposable diaper 1, it is difficult for the user to feel the stiffness of the compressed regions 14, 15 through the top sheet 2. As a result, a soft texture can be secured and an excellent feeling when being worn can be obtained by the disposable diaper 1 as a whole.

In the first embodiment, the absorbent body 4 includes the recessed portions 22 in the base portions 13, however, in the absorbent body in the embodiment to be explained in the following, a configuration which corresponds to the recessed portion is not present.

Figure 8:
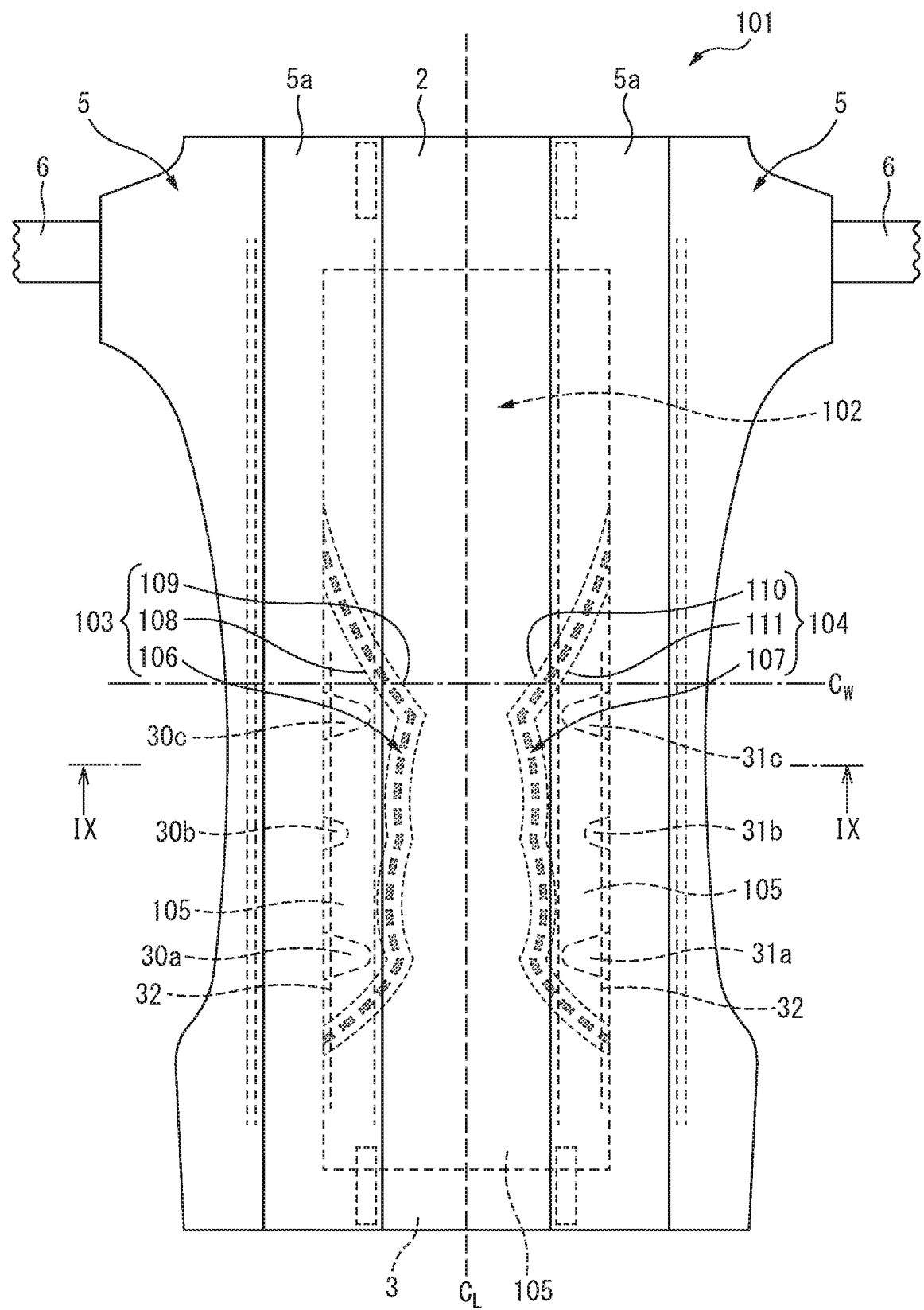
FIG. 8 is a plan view which schematically shows an expanded state of a second embodiment of the disposable diaper as the absorbent article according to the present invention.
Figure 9:
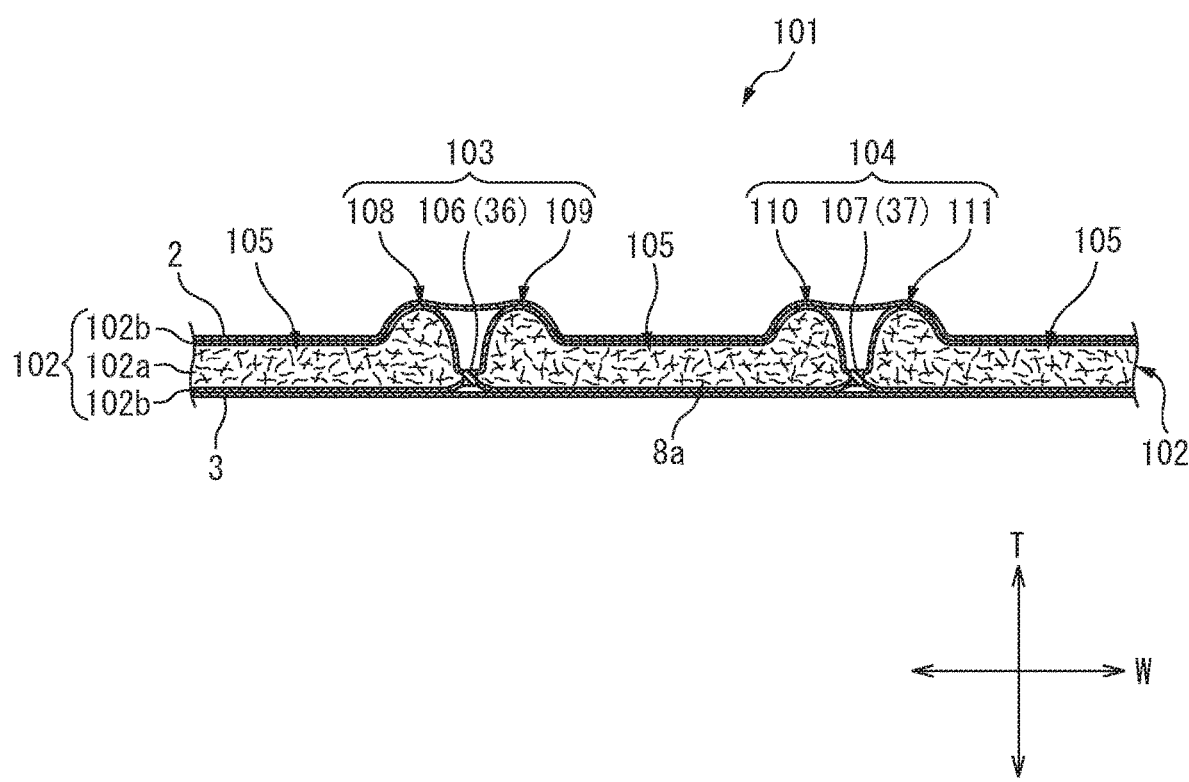
FIG. 9 is a schematic main portion enlarged end view along IX-IX line shown FIG. 8.

That is, FIGS. 8 and 9 show a disposable diaper 101 as an absorbent article according to the second embodiment of the present invention, and the absorbent body 102 of the disposable diaper 101 as a whole includes the deformation guiding portions 103, 104 which extend in the longitudinal direction of the disposable diaper 101, and the base portions 105 which are disposed on both sides of the deformation guiding portions 103, 104. Further, the deformation guiding portions 103, 104 include the compressed regions 106, 107 which extend in the same direction as the longitudinal direction of the deformation guiding portions 103, 104 and in which the absorbent body 102 is compressed in the thickness direction, that is, compacted, and the protruded portions 108 to 111 which as a whole extend in the longitudinal direction of the compressed regions 106, 107 on both sides of the compressed regions 106, 107, and protrude from the base portions 105 toward the skin surface side.

Incidentally, since the disposable diaper 101 as the absorbent article according to the second embodiment has the same configurations as those in the first embodiment except for the configuration of the absorbent body 102, and achieves the same operations and effects, the same reference numerals are allotted and the detailed descriptions are omitted. Further, since the deformation guiding portions 103, 104 in the absorbent body 102 have the configuration which is substantially the same as that of the deformation guiding portions 11, 12 in the first embodiment, except for the feature that the absorbent polymers are hardly included as described below, and achieve the same operations and effects, the detailed descriptions thereof, including the compressed regions 106, 107 which configure the deformation guiding portions 103, 104 (which correspond to the compressed regions 14, 15 in the first embodiment) and the protruded portions 108 to 111 (which correspond to the protruded portions 16 to 19 in the first embodiment), are omitted.

In the base portions 105, the entire surface on the skin surface side is formed into a substantially flat surface, and the base portions 105 as a whole have a substantially constant thickness. Accordingly, in the base portions 105, the portions which correspond to the recessed portions 22 in the first embodiment are not present. Since the entire surface on the skin surface side of the base portions 105 is formed into a substantially flat surface, unevenness can hardly be felt when the base portions 105 come in contact with the skin through the top sheet 2, and it is easy for the base portions 105 to fit on the skin.

Further, the absorbent body 102 of the present embodiment includes an absorbent core 102a and a core wrapping sheet 102b which covers the absorbent core 102a. The absorbent core 102a hardly includes the absorbent polymers, and is formed basically by a water absorbent fiber such as pulp, etc. Accordingly, since the water absorbent fibers 8a which are softer than the absorbent polymers are included by a large amount, the absorbent core 102a as a result has an improved softness in the entire base portions 105, compared to the case in which the absorbent polymers are included.

The following method may be used when manufacturing the disposable diaper 101 which has the above mentioned configuration.

Figure 10:
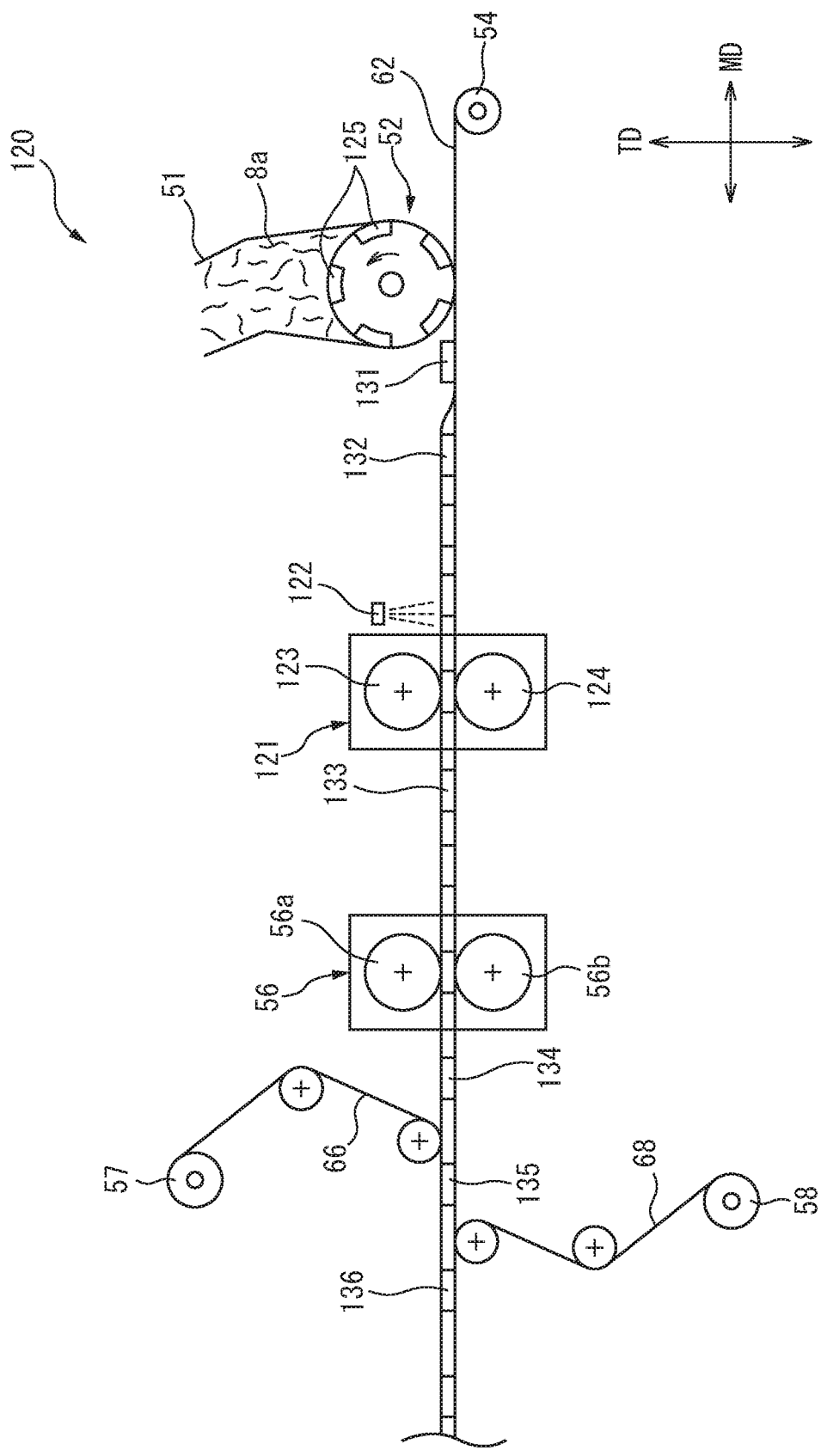
FIG. 10 is a schematic view of a manufacturing apparatus to be used in a manufacturing method of the absorbent article of the second embodiment according to the present invention.

That is, FIG. 10 shows one example of a manufacturing apparatus to manufacture the disposable diaper 101 according to the second embodiment. The manufacturing apparatus 120 is different from the manufacturing apparatus 50 used for manufacturing the disposable diaper 1 according to the first embodiment, in that the portion of the pressing device is different, and that instead of the pressing device, the manufacturing apparatus 120 has a configuration of including a shaping device 121 which shapes an object to a predetermined shape. Further, at the further upstream in the conveying direction MD of the shaping device 121, a moisture supplying device 122 is provided which supplies moisture, such as water, etc., for the later described second laminated body 132 which is the object of shaping.

Figure 11:
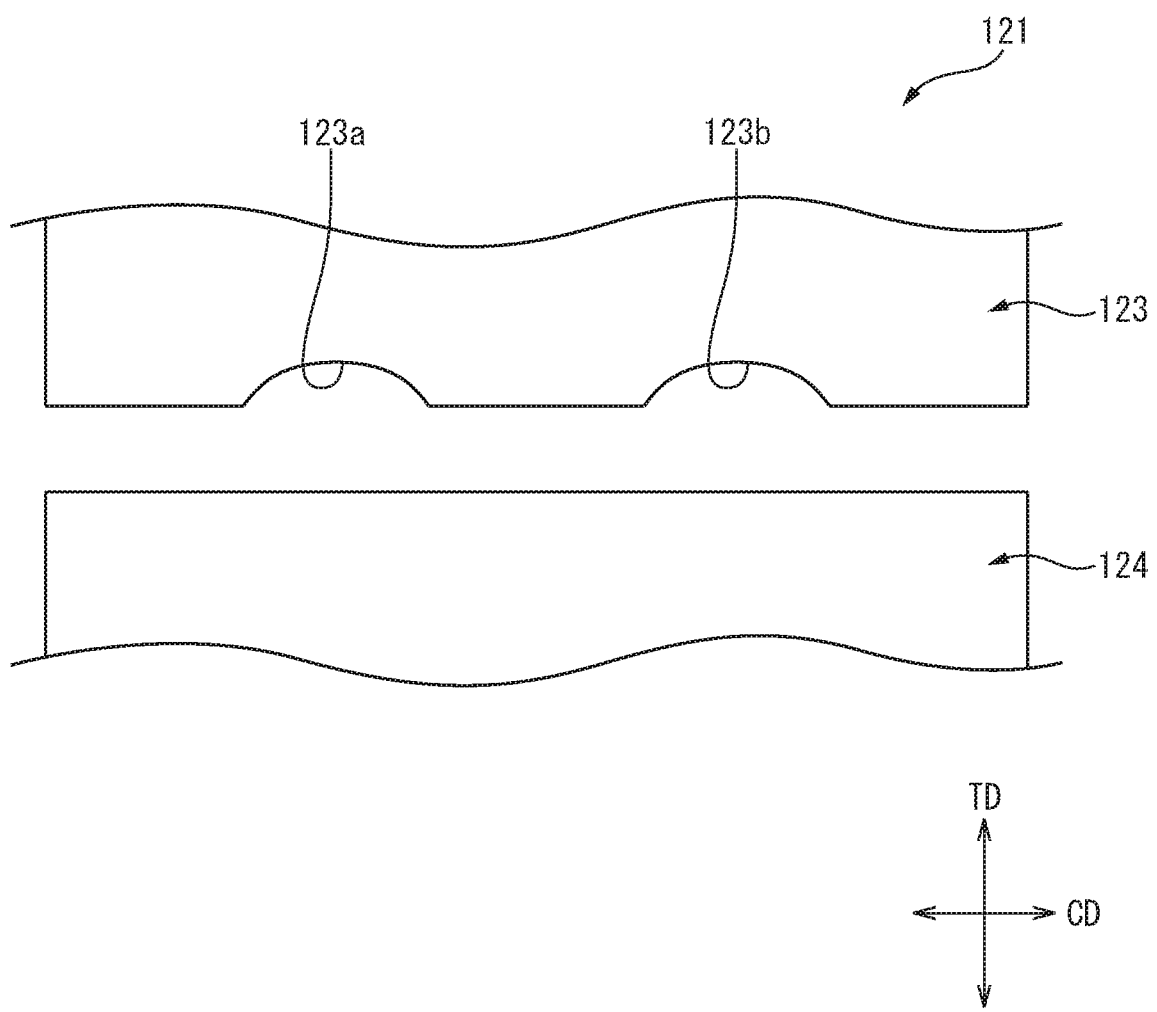
FIG. 11 is a main portion enlarged end view which schematically shows a portion to which an outer circumferential surface of a pair of shaping rolls in a shaping device that configures the manufacturing apparatus of FIG. 10 faces.

The shaping device 121 includes a pair of upper and lower rolls 123, 124, and as shown in FIG. 11, the upper side roll 123 is a shaping roll, and includes, on the outer circumferential surface thereof, a pair of grooves 123a, 123b which shape a pair of protruded portions 137, 138 which are the portions corresponding to the deformation guiding portions 103, 104 before the compressed regions 106, 107 are formed (which also correspond to the protruded portions 81, 82 in the first embodiment) and extend in the circumferential direction. The pair of grooves 123a, 123b have the shape and width in the longitudinal direction adapted to the deformation guiding portions 103, 104, at positions adapted to the positions of the deformation guiding portions 103, 104. On the other hand, the lower side roll 124 is an anvil roll in which the outer circumferential surface is flat. Further, by passing the second laminated body 132 which is the object through between the pair of rolls 123, 124, the respective pair of protruded portions 137, 138 can be shaped on one surface (in this case, the upper surface) of the second laminated body 132. Further, the shaping device 121 is configured to be capable of heating the rolls 123, 124, and of shaping the second laminated body 132 while being heated.

Further, in the present embodiment, since the absorbent polymers are not included in the absorbent body 102, as shown in FIG. 10, the absorbent material to be supplied to the suction drum 52 through the conveying tube 51 is basically the opened water absorbent fibers 8a only. Further, portions which correspond to the protrusions 53a, 53b of the molding member 53 of the first embodiment are not provided in the molding member 125 of the suction drum 52, and the molding member 125 has a flat bottom portion. Accordingly, the later described first laminated body 131 which is laminated inside the molding member 125 is formed into a substantially rectangular parallelepiped shape.

Incidentally, since the configurations of the manufacturing apparatus 120 according to the present embodiment are basically the same as those of the manufacturing apparatus 50 according to the first embodiment, except for the configurations of the molding member 125 of the suction drum and of the shaping device 121, and achieve the same operations and effects, the same reference numerals are allotted and the detailed descriptions are omitted.

When manufacturing the disposable diaper 101 by using the above mentioned manufacturing apparatus 120, basically, a first step of forming the first laminated body 131, a second step of covering the first laminated body 131 with the core wrapping sheet continuous body 62 so as to obtain the second laminated body 132, a third step of shaping the second laminated body 132 by the shaping device 121 so as to obtain the third laminated body 133, and a fourth step of compressing the predetermined position of the third laminated body 133 by the compressing device 56, whereby performing the embossing treatment so as to obtain the fourth laminated body 134, are sequentially performed. Further, a fifth step of laminating the top sheet continuous body 66 onto the fourth laminated body 134 so as to obtain the fifth laminated body 135, and a sixth step of joining the back sheet continuous body 68 to the fifth laminated body 135 so as to obtain the sixth laminated body 136, are sequentially performed.

In the first step, since the absorbent material to be supplied to the suction drum 52 through the conveying tube 51 is the opened water absorbent fibers 8a, the first laminated body 131 which is formed by the first step as a whole is formed by water absorbent fibers with a substantially uniform basis weight. Since other configurations of the first laminated body 131 are the same as those in the first embodiment, the detailed descriptions are omitted. Further, since the second step is basically the same as that in the first embodiment, the detailed descriptions are omitted.

In the third step, the second laminated body 132 as shown in FIG. 12(a) which has been formed in the second step, that is, the material configured by the first laminated body 131 formed by the water absorbent fibers 8a, and the core wrapping sheet continuous body 62 which covers the first laminated body 131, is shaped so as to obtain the third laminated body 133.

To be more specific, water, etc., is jetted to the second laminated body 132 by the moisture supplying device 122 so as to moisten the water absorbent fibers 8a, and then the moistened second laminated body 132 is passed through between the heated pair of rolls 123, 124 in the shaping device 121, so as to form the pair of protruded portions 137, 138. That is, by passing the moistened second laminated body 132 through between the heated pair of rolls, the adjacent ones among the water absorbent fibers 8a which form the first laminated body 131 are to be bonded with each other by hydrogen bonding, whereby the second laminated body 132 is shaped in a state in which the pair of protruded portions 137, 138 which protrude toward above in accordance with the shape of the pair of grooves 123a, 123b of the roll 123 which is positioned on the upper side. Incidentally, the portions shaped by the portions other than the pair of grooves 123a, 123b are to be the portions which correspond to the base portions 105 of the absorbent body 102.

As a result, as shown in FIG. 12(b), the third laminated body 133 in a state in which the portions which correspond to the base portions 105 of the absorbent body 102 and the protruded portions 137, 138 are shaped, is formed.

Incidentally, since the fourth to the sixth steps are basically the same as those in the first embodiment, the detailed descriptions are omitted. Incidentally, the cross section (end face) shape of the sixth laminated body 136 which is formed by the sixth step is substantially the same as the shape shown in FIG. 9.

After the sixth step, the sixth laminated body 136 is cut into the shape of the disposable diaper 101 by a cutting device. Accordingly, the disposable diaper 101 is completed in which the absorbent body 102 includes the deformation guiding portions 103, 104 and the base portions 105 which are disposed on both sides of the deformation guiding portions 103, 104, and the deformation guiding portions 103, 104 include the compressed regions 106, 107 and the protruded portions 108 to 111 which are disposed on both sides of the compressed regions 106, 107.

The disposable diaper 101 which has the above mentioned configurations basically achieves the same effects as those of the disposable diaper 1 according to the first embodiment. However, since the absorbent body 102 is formed only by the water absorbent fibers 8a, it is difficult to sense the granular feeling, and softer texture can be obtained by the water absorbent fibers 8a, compared to the case in which the absorbent polymers are used.

In the first and the second embodiments, the compressed portions 36, 37 are configured by the absorbent core and the core wrapping sheet being compressed, however, in another embodiment of the present invention, the compressed portions are formed by compressing the top sheet together with the absorbent core and the core wrapping sheet from the top sheet side. Accordingly, the surface on the top sheet side of the absorbent article is in a state in which the portions recessed toward the non-skin surface side, that is, the back sheet side by the compressed portions are exposed. In the present embodiment, the top sheet is disposed so as to be in close contact along the outer surface on the skin surface side of the protruded portions in accordance with the protruded shapes of the protruded portions, so that the top sheet and the protruded portions deform substantially at the same time by an outer force. Accordingly, the protruded heights of the protruded portions are to be higher by the thickness of the top sheet, whereby the opportunities for the skin to come in contact with the compressed regions, and especially the compressed portions can be decreased, and when the absorbent article is deformed so as to protrude toward the non-skin surface side, the protruded portions come closer to each other, and cover the compressed regions in which the stiffness is increased by compression, whereby when the skin surface of the user comes in contact with the surface of the absorbent article, and even when being in direct contact with the compressed regions from above the top sheet 2, it is difficult for the stiffness at the compressed regions to be felt.

In the first embodiment, the configuration has been explained in which the base portions include the recessed portions 22, in the case in which the absorbent core 8 includes the water absorbent fibers 8a and the absorbent polymers 8b, however, even in a case in which the absorbent core includes the water absorbent fibers and the absorbent polymers, the base portions may have a configuration of not including the recessed portions in the same manner as in the case in which the absorbent core 102a is configured only by the water absorbent fibers 8a, as in the second embodiment.

Incidentally, when manufacturing an absorbent article in which the base portions have the configuration of not including the recessed portions, the side surface of the protrusions of the molding member has a gentler slope compared to the side surface of the protrusions of the molding member in the first embodiment. In this case, the absorbent polymers which have bounced back from the upper base of the molding member may further collide with and bounce back from the sides of the molding member before reaching the bottom portion. Accordingly, the absorbent polymers are dispersed to a wider range in the bottom portion of the molding member and it is difficult for the difference between the recovery of the thickness of the recessed portions and the recovery of the thickness of the base portions other than the recessed portions after the compressing step to be occurred, whereby it is difficult for the portions which correspond to the above mentioned recessed portions to be formed, compared to the case in which the sides of the protrusions are steep.

Further, by suitably modifying the slope of the sides of the molding member, the mass inclusion ratio of the absorbent polymers included in the portions which extend in the thickness direction on the non-skin surface side of the recessed portions can be adjusted to have a desired value.

In the first and the second embodiments, the deformation guiding portions 11, 12, 103, 104 are provided so as to sandwich the axis line in the longitudinal direction of the absorbent body 4, 102, at positions mutually being separated from each other, however, there may be only one deformation guiding portion.

Further, in the deformation guiding portions 11, 12, 103, 104, the compressed regions 14, 15, 106, 107 are provided at the substantially central portions in the width direction of the deformation guiding portions 11, 12, 103, 104, however, the compressed regions may be provided at portions other than the central portions in the width direction of the deformation guiding portions, as long as the protruded portions are reliably formed on both sides in the longitudinal direction of the compressed regions.

Further, in one deformation guiding portion, the protruded portions have substantially the same protruded height in the drawings, however, the protruded portions may have different heights. Further, a protruded portion may have a protruded height different from that of a protruded portion in another deformation guiding portion. Still further, the shape in a plan view of a deformation guiding portion (which is the shape viewed from the thickness direction) may be different from the shape depicted in the drawings.

In the first and the second embodiments, the compressed regions 14, 15, 106, 107 have a configuration of including the compressed portions provided intermittently and serially, and the non-compressed portions between the adjacent compressed portions, however, the compressed regions may be configured so that the compressed portions, that is, the compacted portions are continuous in the longitudinal direction of the compressed regions.

In the first and the second embodiments, an example of a disposable diaper as an absorbent article has been explained, however, the absorbent article may be various types of absorbent articles, such as a sanitary napkin, an incontinence pad (a panty liner), etc.

The invention claimed is:

1. An absorbent article which has a longitudinal direction, a width direction, and a thickness direction, and comprises an absorbent body that includes at least a water absorbent fiber, wherein
   the absorbent body includes a deformation guiding portion which extends in a predetermined direction, and base portions which are disposed on both sides of the deformation guiding portion,
   the deformation guiding portion includes
      a compressed region which extends in the predetermined direction and in which the absorbent body is compacted in the thickness direction, and
      protruded portions which extend in the predetermined direction on both sides of the compressed region and protrude from the base portions toward a skin surface side,
   wherein a thickness of each of the base portions is greater than a thickness of the compressed region, and
   a fiber density of the protruded portions is lower than a fiber density of the base portions.

2. The absorbent article according to claim 1, wherein
   the predetermined direction is the longitudinal direction, and
   the absorbent body includes two deformation guiding portions so as to sandwich a central longitudinal axis line of the absorbent body, at positions mutually being separated from each other.

3. The absorbent article according to claim 2, wherein
   the absorbent body has a longitudinal direction, a width direction, and a thickness direction, and includes an absorbent core which includes at least the water absorbent fiber, and a core wrapping sheet which covers an outer circumferential surface of the absorbent core,
   the absorbent core includes a plurality of parallel bending guiding lines spaced apart from each other in the longitudinal direction, each bending guiding line connects a pair of notch portions provided at opposite end portions of the absorbent core in the width direction, and
   the deformation guiding portions extend over at least a distance between the bending guiding lines that are spaced farthest from each other in the longitudinal direction.

4. The absorbent article according to claim 1, wherein a width of the compressed region is ½ or shorter of a width of the deformation guiding portion.

5. The absorbent article according to claim 1, wherein the compressed region includes
   a plurality of compressed portions which are provided intermittently and serially in the predetermined direction, and
   non-compressed portions each of which is provided between adjacent compressed portions among the plurality of compressed portions.

6. The absorbent article according to claim 1, wherein
   the absorbent body includes absorbent polymers, and
   a basis weight of the absorbent polymers included in the deformation guiding portion is less than a basis weight of the absorbent polymers included in the base portions.

7. The absorbent article according to claim 1, wherein each of the base portions includes a recessed portion recessed toward a non-skin surface side, and the recessed portion is provided adjacent to one of the protruded portions along a longitudinal direction of the protruded portion.

8. The absorbent article according to claim 7, wherein
   the absorbent body includes absorbent polymers, and
   a mass inclusion ratio of the absorbent polymers included in a portion which extends in the thickness direction of the recessed portion in each of the base portions is more than a mass inclusion ratio of the absorbent polymers included elsewhere in the absorbent body.

* * * * *